US006264937B1

(12) United States Patent
Mandeville, III et al.

(10) Patent No.: US 6,264,937 B1
(45) Date of Patent: Jul. 24, 2001

(54) FAT-BINDING POLYMERS

(75) Inventors: W. Harry Mandeville, III, Lynnfield; George M. Whitesides, Newton; Stephen Randall Holmes-Farley, Arlington, all of MA (US)

(73) Assignee: GelTex Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 09/166,453

(22) Filed: Oct. 5, 1998

Related U.S. Application Data

(63) Continuation-in-part of application No. 09/004,963, filed on Jan. 9, 1998, now abandoned.

(51) Int. Cl.$^7$ ...................... A61K 31/785; A61K 31/765; A61K 31/335; A61K 31/74
(52) U.S. Cl. ...................... 424/78.35; 424/78.17; 424/78.37; 514/449
(58) Field of Search ............... 514/449; 424/78.17, 424/78.18, 78.31, 78.35, 78.37

(56) References Cited

U.S. PATENT DOCUMENTS

| | | | |
|---|---|---|---|
| 3,780,171 | 12/1973 | Irmscher et al. | 424/79 |
| 3,923,972 | 12/1975 | Fields et al. | 424/78 |
| 4,160,826 | 7/1979 | Fischetti | 424/180 |
| 4,211,765 | 7/1980 | Johnson et al. | 424/78 |
| 4,218,443 | 8/1980 | Comai et al. | 424/181 |
| 4,265,879 | 5/1981 | Fields et al. | 424/78 |
| 4,302,450 | 11/1981 | Comai et al. | 424/181 |
| 4,432,968 | 2/1984 | Page et al. | 424/78 |
| 4,598,089 | 7/1986 | Hadvary et al. | 514/449 |
| 4,959,179 | 9/1990 | Aronson et al. | 252/135 |
| 5,063,210 | 11/1991 | Lange, III et al. | 514/54 |
| 5,089,163 | 2/1992 | Aronson et al. | 252/135 |
| 5,137,716 | 8/1992 | Weisenfeld | 424/78.01 |
| 5,200,183 | 4/1993 | Tang et al. | 424/94.6 |
| 5,286,481 | 2/1994 | Weisenfeld | 424/78.01 |
| 5,308,766 | 5/1994 | Dennis et al. | 435/184 |
| 5,376,674 | 12/1994 | Derungs et al. | 514/422 |
| 5,401,498 | 3/1995 | Kesseler et al. | 424/78.11 |
| 5,427,919 | 6/1995 | Dennis et al. | 435/18 |
| 5,453,282 | 9/1995 | Kanauchi et al. | 424/464 |
| 5,453,429 | 9/1995 | Bliem et al. | 514/288 |
| 5,474,993 | 12/1995 | Rubin et al. | 514/192 |
| 5,484,777 | 1/1996 | Lange, III et al. | 514/54 |
| 5,567,597 | 10/1996 | Dennis et al. | 435/18 |
| 5,569,452 | 10/1996 | Amidon et al. | 424/78.1 |
| 5,597,810 | 1/1997 | Hoffman et al. | 514/54 |
| 5,607,669 | 3/1997 | Mandeville, III et al. | 424/78.12 |
| 5,618,530 | 4/1997 | Mandeville, III et al. | 424/78.12 |
| 5,624,963 | 4/1997 | Mandeville, III et al. | 514/789 |
| 5,665,348 | 9/1997 | Okayama et al. | 424/78.35 |
| 5,679,717 | 10/1997 | Mandeville, III et al. | 514/742 |
| 5,693,675 | 12/1997 | Mandeville, III et al. | 514/742 |
| 5,703,188 | 12/1997 | Mandeville, III et al. | 526/290 |
| 5,750,524 | 5/1998 | Mera et al. | 514/247 |
| 5,900,233 | 5/1999 | Day | 424/78.01 |
| 5,900,475 | 5/1999 | Mandeville et al. | 528/392 |

FOREIGN PATENT DOCUMENTS

| | | |
|---|---|---|
| 0 050 347 | 4/1982 | (EP) . |
| 0050 347 | 4/1982 | (EP) . |
| 0 381 262 | 8/1990 | (EP) . |
| 2 081 400 | 12/1971 | (FR) . |
| 6-321787 | 11/1994 | (JP) . |
| WO 89/07455 | 8/1989 | (WO) . |

OTHER PUBLICATIONS

CA 127:156561, James et al., 1997.*
CA 124:105377, Drent et al., 1995.*
Gargouri, Y., et al., "Ajoene prevents fat digestion by human gastric lipase in vitro," *Biochimica et Biophysica Acta.* 1006:137–139 (1989).
Gargouri, Y., et al., "Covalent inhibition of digestive lipases: an in vitro study," *Biochimica et Biophysica Acta.* 1344:6–37 (1997).
Karamać, M. and Amarowicz, R., "Inhibition of Pancreatic Lipase by Phenolic Acids, Examination in vitro," *Verlag der Zeitschrift für Naturforschung*:903–905 (1996).
Marguet, F., et al., "Digestive lipases: inactivation by phosphonates," *Biochimica et Biophysica Acta.* 1210:157–166 (1994).
Mannesse, M.L.M., et al., "Phosphonate analogues of triacylglycerols are potent inhibitors of lipase," *Biochimica et Biophysica Acta.* 1259:56–64 (1995).
Martichonok, V. and Jones, J.B., "(Z)–Heptadec–8–enylboronic acid: a potential lipase inhibitor," *J. Chem. Soc. Perkin Trans.* I:2927–2929 (1995).
Vainio, P., et al., "Inhibition of Lipoprotein Lipase by Benzene Boronic Acid Effect of Apolipoprotein C–II," *Biochimica et Biophysica Acta.* 711:386–390 (1982).
Bagree, A., et al., "Modification of ε–Amino Group of Lysine in Proteins by Acylation with Pyromellitic Dianhydride and o–Sulphobenzoic Anhydride," *FEBS Letters* 120(2):275–277 (1980).
Stadler, P., et al., "Inhibition of microbial lipases with stereoisomeric triradylglycerol analog phosphonates," *Biochimica et Biophysica Acta.* 1304:229–244 (1996).

(List continued on next page.)

*Primary Examiner*—Russell Travers
*Assistant Examiner*—S. Wang
(74) *Attorney, Agent, or Firm*—Hamilton, Brook, Smith & Reynolds, P.C.

(57) ABSTRACT

The present invention relates to a method for treating obesity, a method for reducing the absorption of dietary fat, and a method for treating hypertriglyceridemia in a patient and to particular polymers for use in the methods or in a manufacture of a medicament. The methods comprise the step of orally administering to a mammal, such as a human, a therapeutically effective amount of one or more fat-binding polymers. The administration of the fat-binding polymer of the invention facilitates the removal of fat from the body prior to digestion, with minimal side effects and low toxicity. In a preferred embodiment, the one or more fat-binding polymers are administered in combination with one or more lipase inibitors, for example, lipstatin and tetrahydrolipstatin.

31 Claims, No Drawings

OTHER PUBLICATIONS

Kawaguchi, K., et al., "Hesperidin as an Inhibitor of Lipases from Procine Pancreas and *Pseudomonas*," *Biosci. Biotech. Biochem.* 61(1):102–104 (1997).

Bochenek, W.J. and Rodgers, J.B., "Effect of Polyol Detergents on Cholesterol and Triglyceride Absorption," *Biochimica et Biophysica Acta* 489:503–506 (1977).

Comai, K. and Sullivan, A.C., "Antiobesity activity of pluronic L–101," *International Journal of Obesity* 4:33–42 (1980).

Han, L–K, et al., "Reduction in fat storage during chitin––chitosan treatment in mice fed a high–fat diet," *International Journal of Obesity* 23:174–179 (1999).

Atkinson et al. "Combined Drug Treatment of Obesity," *Obesity Research*, vol. 3, No. S4:497S–500S (1995).

Sjöström et al., "Randomised placebo–controlled trial of orlistat for weight loss and prevention of weight regain in obese patients," *The Lancet*, 352:167–172 (1998).

\* cited by examiner

FAT-BINDING POLYMERS

RELATED APPLICATIONS

This application is a Continuation-in-Part of U.S. application Ser. No. 09/004,963 filed on Jan. 9, 1998, now abandoned the entire content of which is hereby incorporated by reference.

BACKGROUND OF THE INVENTION

Human obesity is a recognized health problem with approximately 97 million people considered clinically overweight in the United States. The accumulation or maintenance of body fat bears a direct relationship to caloric intake. Therefore, one of the most common methods for weight control to combat obesity is the use of relatively low-fat, low calorie diets, that is, diets containing less fat and calories than a "normal diet" or that amount generally consumed by the patient.

The presence of fats in a great many food sources greatly limits the food sources which can be used in a low-fat diet. Additionally, fats contribute to the flavor, appearance and physical characteristics of many foodstuffs. As such, the acceptability of low-fat diets and the maintenance of such diets are difficult.

Various chemical approaches have been proposed for controlling obesity. Anorectic agents, such as dextroamphetamine, the combination of the non-amphetamine drugs phentermine and fenfluramine ("Phen-Fen") and dexfenfluramine (Redux) alone, are associated with serious side effects. Indigestible materials such as OLESTRA™, mineral oil or neopentyl esters (see U.S. Pat. No. 2,962,419) have been proposed as substitutes for dietary fat. Garcinia acid and derivatives thereof have been described as treating obesity by interfering with fatty acid synthesis. Swellable crosslinked vinyl pyridine resins have been described as appetite suppressants via the mechanism of providing non-nutritive bulk, as in U.S. Pat. No. 2,923,662. Surgical techniques, such as temporary ileal bypass surgery, are employed in extreme cases.

However, methods for treating obesity, such as those described above, have serious shortcomings with controlled diet remaining the most prevalent technique for controlling obesity. As such, new methods for treating obesity are needed.

SUMMARY OF THE INVENTION

The present invention relates to a method for treating obesity, a method for reducing the absorption of dietary fat, and a method for treating hypertriglyceridemia in a patient and to particular polymers for use in the methods or in a manufacture of a medicament. The methods comprise the step of orally administering to a mammal, such as a human, a therapeutically effective amount of a fat-binding polymer. The administration of a fat-binding polymer of the invention facilitates the excretion of fat from the body without digestion, with minimal side effects and low toxicity. In a preferred embodiment, the fat-binding polymers are administered in combination with a therapeutically effective amount of a lipase inhibitor, such as the pancreatic lipase inhibitors described in U.S. Pat. No. 4,598,089 to Hadvary et al. The combination administration can reduce undesirable side effects often encountered when lipase inhibitors, in particular, the pancreatic lipase inhibitors lipstatin and tetrahydrolipstatin are administered alone. For example, a serious side effect resulting from the administration of a lipase inhibitor is steatorrhea, or fatty stools.

The fat-binding polymers of the invention comprise at least one fat-binding region. A fat-binding region can include a region having a positive charge, a region which is hydrophobic or a region having a positive charge and which is hydrophobic.

In one embodiment, the fat-binding polymer is an aliphatic polymer selected from the group consisting of polyalkylacrylates, polyacrylamides, polyalkylmethacrylates, polymethacrylamides, poly-N-alkylacrylamides, poly-N-alkylmethacrylamides, substituted derivatives thereof and copolymers thereof. For example, the substituted derivatives of the polymers can be characterized by one or more substituents, such as substituted or unsubstituted, saturated or unsaturated alkyl, and substituted or unsubstituted aryl groups. Suitable substituents to employ on the alkyl or aryl groups include, but are not limited to, cationic or neutral groups, such as alkoxy, aryl, aryloxy, aralkyl, halogen, amine, and ammonium groups. For example, the polymer can be poly (dimethylamino propylacrylamide), poly (trimethylammonium ethylacrylate), poly (trimethylammonium ethyl methacrylate), poly (trimethylammonium propyl acrylamide), poly(dodecyl acrylate), poly(octadecyl acrylate), poly(octadecyl methacrylate) and copolymers thereof.

In another embodiment, the fat binding polymer is a synthetic amine polymer. Amine polymers suitable for use in the invention include, but are not limited to, poly (allylamine), polyethyleneimine, poly(vinylamine), poly (diallylamine), and poly(diallylmethylamine).

In yet another embodiment, the fat-binding polymer is a hydroxyl-containing polymer, for example, poly (vinylalcohol).

In a specific embodiment, the fat-binding polymer is an amine-containing polymer wherein one or more hydrophobic regions are bound to a portion of the amine nitrogens of the amine polymer. In a particular embodiment, between about 1 and about 60 percent of the amine nitrogens are substituted, preferably between about 1 and about 30 percent.

In another embodiment, the hydrophobic region of the fat-binding polymer can include a hydrophobic moiety, for example, a substituted or unsubstituted, normal, branched or cyclic alkyl group having at least four carbons. In a particular embodiment, the hydrophobic moiety is an alkyl group of between about four and thirty carbons.

In another embodiment, the hydrophobic region is a quaternary amine-containing moiety having a terminal hydrophobic substituent. Suitable hydrophobic regions which can include a hydrophobic moiety and/or a quaternary amine-containing moiety are described herein and in U.S. Pat. Nos. 5,607,669, 5,679,717 and 5,618,530, the entire contents of which are incorporated herein by reference in their entirety.

In yet another embodiment, the fat-binding polymer is substituted by a lipase inhibitor such as those described in U.S.S.N. 09/005,379 filed on Jan. 9, 1998, and Ser. No. 09/166,510 (Attorney Docket No. (TX96-11A) entitled "Lipase Inhibiting Polymers" being filed concurrently herewith, the entire contents of which are incorporated herein by reference.

The polymers of the present invention offer desirable pharmacological properties such as excellent fat binding properties and low toxicity. In addition, when the fat-binding polymers are administered in combination with lipase inhibitors, as described herein, undesirable side effects experienced, such as steatorrhea, when the lipase inhibitors are administered alone can be lessened.

DETAILED DESCRIPTION OF THE INVENTION

The features and other details of the invention will now be more particularly described and pointed out below as well as in the claims. It will be understood that the particular embodiments of the invention are shown by way of illustration and not as limitations of the invention. The principle features of this invention can be employed in various embodiments without departing from the scope of the invention.

In one aspect, the invention relates to a method for treating obesity comprising the step of orally administering to a mammal a therapeutically effective amount of one or more fat-binding polymers. In a preferred embodiment, the fat-binding polymer is administered in combination with a therapeutically effective amount of a lipase inhibitor.

In another aspect, the invention relates to a method for reducing the absorption of dietary fat comprising the step of orally administering to a mammal a therapeutically effective amount of one or more fat-binding polymers. In a preferred embodiment, the fat-binding polymer is administered in combination with a therapeutically effective amount of a lipase inhibitor.

In yet another aspect, the invention relates to a method for treating hypertriglyceridemia in a mammal comprising the step of orally administering to a mammal a therapeutically effective amount of one or more fat-binding polymers. In a preferred embodiment, the fat-binding polymer is administered in combination with a therapeutically effective amount of a lipase inhibitor.

A particular aspect of the invention relates to a method for treating steatorrhea comprising the step of orally administering to a mammal a therapeutically effective amount of a fat-binding polymer. In a specific embodiment, the steatorrhea is a result of the administration of a lipase inhibitor.

The invention also relates to fat-binding polymers useful in the method of the invention.

"Lipases" as that term is used herein, are ubiquitous enzymes which hydrolyze ester bonds in neutral lipids. Examples of lipases include, but are not limited to, pancreatic and gastric lipases. The preferred substrates of lipases are insoluble in water. Lipases exhibit maximal activity in the presence of lipid/water interfaces. For example, pancreatic lipase, which is the key enzyme of dietary triglyceride absorption, exerts it activity at the water/lipid interface, in conjunction with bile salts and co-lipase.

"Lipase inhibitor" as that term is used herein refers to compounds which are capable of inhibiting the action of lipases, for example, gastric and pancreatic lipases. Lipstatin and its tetrahydro derivative, Tetrahydrolipstatin, as described in U.S. Pat. No. 4,598,089 to Hadvary et al., the entire content of which is hereby incorporated by reference, are potent inhibitors of both gastric and pancreatic lipases, as well as cholesterol ester hydrolase. Lipstatin is a natural product of microbial origin, and tetrahydrolipstatin is the result of catalytic hydrogenation of lipstatin. Other lipase inhibitors include a class of compound commonly referred to as Panclicins. Panclicins are analogues of Tetrahydrolipstatin (See e.g., Mutoh, M., et al., "Panclicins, Novel Pancreatic Lipase Inhibitors, II. Structural Elucidation," *The Journal of Antibiotics*, 47(12): 1376–1384 (1994), the entire content of which is hereby incorporated by reference.)

"Fat-binding polymers", as that term is used herein, are polymers which absorb, bind or otherwise associate with fat thereby inhibiting (partially or completely) fat digestion, hydrolysis, or absorption in the gastrointestinal tract. The fat-binding polymers comprise one or more fat-binding regions. "Fat-binding regions", as defined herein can include a positively charged region, a hydrophobic region, or a region which is both positively charged and hydrophobic.

"Fats", as that term is used herein, are solids or liquid oils generally consisting of glycerol esters of fatty acids. Sources of fats include both animal and vegetable fats, for example, triglyceride esters of saturated and/or unsaturated fatty acids, free fatty acids, diglycerides, monoglycerides, phospholipids and cholesterol esters are fats, as defined herein.

A variety of polymers can be employed in the invention described herein. The polymers are synthetic polymers which can be aliphatic, or aromatic. However, aliphatic and synthetic polymers are preferred. A "synthetic polymer", as that term is employed herein, is a polymer which is not obtainable from a natural source either directly or through a minor derivatization of the naturally occurring form. Further, the polymer can be hydrophobic, hydrophilic or copolymers of hydrophobic and/or hydrophilic monomers. The polymers can be manufactured from olefinic or ethylenic monomers (such as vinylalcohol, allylamine or acrylic acid) or condensation polymers.

For example, the polymers can include polyvinylalcohol, polyvinylamine, poly-N-alkylvinylamine, polyallylamine, poly-N-alkylallylamine, polydiallylamine, poly-N-alkyldiallylamine, polyalkylenimine, other polyamines, polyethers, polyamides, polyacrylic acids, polyalkylacrylates, polyacrylamides, polymethacrylic acids, polyalkylmethacrylates, polymethacrylamides, poly-N-alkylacrylamides, poly-N-alkylmethacrylamides, polystyrene, polyvinylnaphthalene, polyethylvinylbenzene, polyaminostyrene, polyvinylbiphenyl, polyvinylanisole, polyvinylimidazolyl, polyvinylpyridinyl, polydimethylaminomethylstyrene, polytrimethylammonium ethyl methacrylate, polytrimethylammonium ethyl acrylate, and substituted derivatives of the above (e.g., fluorinated monomers thereof) and copolymers thereof. In addition, the polymers can be further characterized by one or more substituents such as substituents, such as substituted and unsubstituted, saturated or unsaturated alkyl, and substituted or unsubstituted aryl groups. Suitable groups to employ include cationic or neutral groups, such as alkoxy, aryl, aryloxy, aralkyl, halogen, amine, and ammonium groups.

Particularly preferred polymers include polyalkylacrylates, polyacrylamides, polyalkylmethacrylates, polymethacrylamnides, poly-N-alkylacrylamides, poly-N-alkylmethacrylamides and copolymers thereof. These polymers can be further characterized by one or more substituents, such as substituted or unsubstituted, saturated or unsaturated alkyl, and substituted or unsubstituted aryl groups. Suitable substituents include cationic or neutral groups, such as alkoxy, aryl, aryloxy, aralkyl, halogen, amine, and ammonium groups, for example.

Other particularly preferred polymers include aliphatic amine polymers, such as polyallylamine, polydiallylamine, polydiallylmethylamine, polyvinylamine, polyethylenimine. In a specific embodiment, the amine polymer comprises one or more hydrophobic regions which are bound to a portion of the amine nitrogens of the amine polymer. In a particular embodiment, between about 1 and about 60 percent of the amine nitrogens are substituted, preferably between about 1 and about 30 percent.

In one embodiment, the hydrophobic region of the fat-binding polymer can include a hydrophobic moiety, for example, a substituted or unsubstituted, normal, branched or cyclic alkyl group having at least four carbons. In a specific embodiment, the hydrophobic moiety is an alkyl group of between about four and thirty carbons.

In another embodiment, the hydrophobic region is a quaternary amine-containing moiety having a terminal hydrophobic substituent.

In yet another embodiment, the fat-binding region comprises a nitrogen, for example, the nitrogen of an amine, capable of possessing a positive charge under conditions present in the gastrointestinal tract. For example, a quaternary amine-containing moiety, or the nitrogen of a polyamine.

In yet another embodiment, the fat-binding polymer is a hydroxyl-containing polymer, for example, poly (vinylalcohol) which can comprise further fat-binding regions. For example, the polymer comprises a repeat unit having the formula

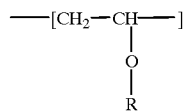

wherein R is a hydrophobic region.

Other polymers and methods of preparation, which can be used in the claimed invention have been reported in the patent literature in, for example, U.S. Pat. Nos. 5,487,888, 5496,545, 5,607,669, 5,618,530, 5,624,963, 5,667,775, and 5,679,717 and co-pending U.S. Applications having Ser. Nos 08/471,747, 08/482,969, 08/567,933,08/659,264, 08/823,699,08/835,857, 081470,940, 08/461,298, 08/826, 197, 08/777,408, 08/927,247, 08/964,956, 08/964,498, and 08/964,536, the entire contents of all of which are incorporated herein by reference.

The polymer can be linear or crosslinked. Crosslinking can be performed by reacting the copolymer with one or more crosslinking agents having two or more functional groups, such as electrophilic groups, which react with, for example, amine groups to form a covalent bond. Crosslinking in this case can occur, for example, via nucleophilic attack of the polymer amino groups on the electrophilic groups. This results in the formation of a bridging unit which links two or more amino nitrogen atoms from different polymer strands. Suitable crosslinking agents of this type include compounds having two or more groups selected from among acyl chloride, epoxide, and alkyl-X, wherein X is a suitable leaving group, such as a halo, tosyl or mesyl group. Examples of such compounds include, but are not limited to, epichlorohydrin, succinyl dichloride, acryloyl chloride, butanedioldiglycidyl ether, ethanedioldiglycidyl ether, pyromellitic dianhydride, and dihaloalkanes. These crosslinking agents are referred to herein as multifunctional crosslinking agents.

The polymer composition can also be crosslinked by including a multifunctional co-monomer as the crosslinking agent in the polymerization reaction mixture. A multifunctional co-monomer can be incorporated into two or more growing polymer chains, thereby crosslinking the chains. Suitable multifunctional co-monomers include, but are not limited to, diacrylates, triacrylates, and tetraacrylates, dimethacrylates, diacrylamides, and dimethacrylamides. Specific examples include ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), pentaerythiitol tetraacrylate, trimethylolpropane triacrylate, bisphenol A dimethacrylate, and bisphenol A diacrylate. Other suitable multifunctional monomers include polyvinylarenes, such as divinylbenzene.

The amount of cross-linking agent is typically between about 0.5 and about 25 weight % based on the combined weight of crosslinking agent and monomers, with 1–20% being preferred. Typically, the amount of cross-linking agent that is reacted with the polymer, when the crosslinking agent is a multifunctional agent, is sufficient to cause between about 0.1 and 20 percent of the nucleophiles present on the monomer, for example, an amine to react with the crosslinking agent. In a preferred embodiment, between about 3 and 15 percent of the nucleophilic sites, for example, amines react with the multifunctional crosslinking agent.

The hydrophobic region or regions of the fat-binding polymers include but are not limited to, for example, a hydrophobic moiety such as a substituted or unsubstituted, normal, branched or cyclic alkyl group having at least about four carbons. For example, a hydrophobic moiety such as an alkyl group of at least four carbons can be bound to the fat-binding polymer, for example, through an amine of the fat-binding polymer.

A "hydrophobic moiety", as the term is used herein, is a moiety which, as a separate entity, is more soluble in octanol than water. For example, the octyl group ($C_8H_{17}$) is hydrophobic because its parent alkane, octane, has greater solubility in octanol than in water. The hydrophobic moieties can be a saturated or unsaturated, substituted or unsubstituted hydrocarbon group. Such groups include substituted and unsubstituted, normal, branched or cyclic alkyl groups having at least four carbon atoms, substituted or unsubstituted arylalkyl or heteroarylalkyl groups and substituted or unsubstituted aryl or heteroaryl groups. Preferably, the hydrophobic moiety includes an alkyl group of between about four and thirty carbons. Specific examples of suitable hydrophobic moieties include the following alkyl groups n-hexyl, n-heptyl, n-octyl, n-nonyl, n-decyl, n-undecyl, n-dodecyl, n-tetradecyl, n-octadecyl, 2-ethylhexyl, 3-propyl-6-methyl decyl and combinations thereof. Other examples of suitable hydrophobic moieties include haloalkyl groups of at least six carbons (e.g., 10-halodecyl), hydroxyalkyl groups of at least six carbons (e.g., 11-hydroxyundecyl), and aralkyl groups (e.g., benzyl).

The positively charged region or regions of the fat-binding polymers include but are not limited to, for example, an amine nitrogen capable of possessing a positive charge under conditions present in the gastro-intestinal tract and a quaternary amine-containing moiety. Suitable quaternary amine-containing moieties include alkyl trialkylammonium groups also referred to as ammonioalkyl groups. The term, "ammonioalkyl", as used herein, refers to an alkyl group which is substituted by a nitrogen bearing three additional substituents. Thus, the nitrogen atom is an ammonium nitrogen atom which bears an alkylene substituent, which links the ammonium nitrogen atom to the polymer, and three additional terminal alkyl substituents having from about one to about twenty-four carbons. A "terminal substituent" of the quaternary amine-containing moiety, as the term is employed herein, is any one of the three substituents on the quaternary amine nitrogen which is not the carbon chain between the polymer backbone and the nitrogen of the quaternary ammonium center. In a specific embodiment, the polymer is an amine polymer and the alkylene group links the ammonium nitrogen atom to the nitrogen atom of the polymer. It is to be understood that multiple moieties can be bound to the same amine and/or different amines of the polymer composition.

In another embodiment, the quaternary amine-containing moiety can bear at least one terminal hydrophobic alkyl substituent, such as an alkyl group having between about four and twenty-four carbons, thereby providing both a hydrophobic region and a positively charged region in combination.

An ammonioalkyl group will further include a negatively charged counterion, such as a conjugate base of a pharmaceutically acceptable acid. Examples of suitable counterions include $Cl^-$, $PO_4^-$, $Br^-$, $CH_3SO_3^-$, $HSO_4^-$, $SO_4^{2-}$, $HCO_3^-$, $CO_3^{2-}$, acetate, lactate, succinate, propionate, butyrate, ascorbate, citrate, maleate, folate, an amino acid derivative, and a nucleotide.

Suitable ammonioalkyl groups are of the general formula:

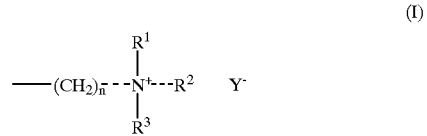

(I)

wherein, $R^1$, $R^2$ and $R^3$ represent an alkyl group, wherein each $R^1$–$R^3$, independently, is a normal or branched, substituted or unsubstituted alkyl group having a carbon atom chain length of between about one to about twenty-four carbon atoms, n is an integer having a value of two or more and Y is a negatively charged counterion. In a particular embodiment, $R^1$, $R^2$ and $R^3$ are all methyl groups and n is an integer between about 2 and about 12 (e.g., 2, 3, 4, 5, 6, 7, 8, 9, 10, 11, or 12).

The alkyl group, which provides the alkylene linking group between the polymer, for example, and the amine of the amine-containing monomer or repeat unit, and the ammonium nitrogen of the alkyl trialkylammonium group, is two or more carbon atoms in length. Examples of preferred alkylene linking groups are ethyl, propyl, butyl, pentyl, hexyl, octyl, and decyl groups. Example of suitable quaternary amine-containing moieties include, but are not limited to:

3-(trimethylammonio)propyl;
4-(trimethylammonio)butyl;
6-(trimethylammonio)hexyl;
8-(trimethylammonio)octyl;
10-(trimethylammonio)decyl;
12-(trimethylammonio)dodecyl and combinations thereof. A particularly preferred amine-containing moiety is a 6-(trimethylammonio)hexyl group.

Alternatively, a quaternary amine-containing moiety and a hydrophobic moiety are present in the same substituent, thereby providing both a positively charged and hydrophobic region in combination. For example, the quaternary amine nitrogen or ammonium nitrogen of the quaternary amine-containing moiety is bound to the polymer backbone by an alkylene having two or more carbons. However, at least one of the three terminal substituents ($R^1$, $R^2$ and $R^3$) of the ammonium nitrogen is a hydrophobic alkyl group having from four to about twenty-four carbons. The remaining terminal substituents are each independently a normal or branched, substituted or unsubstituted alkyl group having from one to about twenty-four carbons or a hydrogen atom. In another embodiment, at least two of the three terminal substituents can be hydrophobic alkyl groups having from four to about twenty-four carbons, the remainder having from one to about twenty-four carbons or a hydrogen atom. In a further embodiment, all three of the terminal substituents can be hydrophobic alkyl groups having from six to about twenty-four carbons.

A "hydrophobic alkyl group", as that term is employed herein, includes a substituted or unsubstituted alkyl group having from four to about twenty-four carbons and which is hydrophobic, as earlier defined. The hydrophobic alkyl group can be, for example, a normal or branched, substituted or unsubstituted alkyl group having from six to about twenty-four carbons.

Particular examples of quaternary amine-containing moieties, which provide both a hydrophobic and quaternary amine-containing substituent, include, but are not limited to:

4-(dioctylmethylammonio)butyl;
3-(dodecyldimethylammonio)propyl;
3-(octyldimethylammonio)propyl;
3-(decyldimethylammonio)propyl;
5-(dodecyldimethylammonio)pentyl;
6-(dimethyldecylammonio)hexyl;
6-(decyldimethylammonio)hexyl;
3-(tridecylammonio)propyl;
3-(docosyldimethylammonio)propyl;
6-(docosyldimethylammonio)hexyl;
4-(dodecyldimethylammonio)butyl;
3-(octadecyldimethylammonio )propyl;
3-(hexyldimethylammonio)propyl;
3-(methyldioctylammonio)propyl;
3-(didecylmethylammonio)propyl;
3-(heptyldimethylammonio)propyl;
3-(dimethylnonylammonio)propyl;
6-(dimethylundecylammonio)hexyl;
4-(heptyldimethylammonio)butyl;
4-(dioctylmethylammonio)butyl;
6-(octyldimethylammonio)hexyl;
12-(decyldimethylammonio)dodecyl;
3-(dimethylundecylammnio)propyl; and
3-(tetradecyldimethylammonio)propyl.

Other suitable quaternary amine-containing moieties include secondary and tertiary analogs, such as 4-(dioctylmethylammonio)4-methylbutyl and 4-(dioctylmethylammonio)-4,4-dimethylbutyl.

The fat-binding polymers of the invention can be formed, for example, by reacting a polymer, which can be linear or crosslinked, with a suitable alkylating agent or by polymerizing an alkylated monomer.

An "acylating agent", as that term is employed herein, means a reactant that, when reacted with a monomer or a copolymer characterized by a repeat unit of the invention and having a nucleophilic site capable of reaction with the acylating agent, causes an acyl substituent, in particular a hydrophobic acyl substituent, as described herein, to be covalently bound to one or more of sites on the fat-binding polymer, for example, the amine nitrogen atoms or hydroxyl oxygens of an amine-containing or hydroxyl-containing monomer or polymer, respectively. Further, when multiple substituents are employed, they can be bound to the same and/or different nucleophilic sites of the fat-binding polymer, for example, the same and/or different amine nitrogens of an amine-containing fat-binding polymer or hydroxyl oxygen of a hydroxyl-containing polymer.

Suitable acylating agents are compounds comprising an acyl group or acyl derivative, for example an anhydride . For example, when the acylating agent is acetic anhydride the nucleophile is modified by addition of an acetyl group. Acylating agents suitable for the addition of a hydrophobic moiety contain an acyl group having at least four carbon atoms, which is bonded to a leaving group such as a halo (e.g., chloro, bromo or iodo). Activated esters are also suitable acylating agents. Examples of suitable acylating agent which provide a hydrophobic moiety include acyl halides having at least four carbon atoms, such as butyryl halide, valeryl halide, hexanoyl halide, heptanoyl halide, octanoyl halide, nonanoyl halide, decanoyl halide, undecanoyl halide, and combinations thereof.

An "alkylating agent", as that term is employed herein, means a reactant that, when reacted with a monomer or a copolymer characterized by a repeat unit of the invention and having a nucleophilic site capable of reaction with the alkylating agent, causes a hydrophobic substituent, as described herein, to be covalently bound to one or more of sites on the fat-binding polymer, for example, the amine nitrogen atoms or hydroxyl oxygens of an amine-containing or hydroxyl-containing monomer or polymer, respectively. Further, when multiple substituents are employed, they can be bound to the same and/or different nucleophilic sites of the fat-binding polymer, for example, the same and/or different amine nitrogens of an amine-containing fat-binding polymer or hydroxyl oxygen of a hydroxyl-containing polymer.

Suitable alkylating agents are compounds comprising an alkyl group or alkyl derivative, having at least four carbon atoms, which is bonded to a leaving group such as a halo (e.g., chloro, bromo or iodo), tosylate, mesylate or epoxy group).

Examples of suitable alkylating agents which provide a hydrophobic moiety include alkyl halides having at least four carbon atoms, such as n-hexyl halide, n-heptyl halide, n-octyl halide, n-nonyl halide, n-decyl halide, n-undecyl halide, n-dodecyl halide, n-tetradecyl halide, n-octadecyl halide, and combinations thereof. Other examples include: a dihaloalkane that includes an alkyl group of at least four carbons (e.g., a 1,10-dihalodecane); a hydroxyalkyl halide having at least four carbon atoms (e.g., an 11 -halo-1-undecanol); an aralkyl halide (e.g., a benzyl halide); an alkyl epoxy ammonium salt having at least six carbons (e.g., glycidylpropyl-trimethylammonium salts) and epoxyalkylamides having at least six carbons (e.g., N-(2,3-epoxypropyl) butyramide or N-(2,3-epoxypropyl) hexanamide). Preferred halogen components of the alkyl halides are bromine and chlorine. Particularly preferred alkylating agents which, when reacted with the polymer composition, will cause formation of an amine polymer reaction product that includes a first substituent, are 1-bromodecane and 1-chlorooctane.

Examples of suitable alkylating agents which can provide a quaternary amine-containing moiety have the general formula:

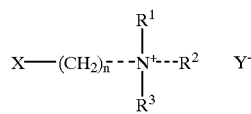

(I)

wherein,
$R^1$, $R^2$, and $R^3$ represent an alkyl group, wherein each R independently is a normal or branched, substituted or unsubstituted alkyl group having a carbon atom chain length of between about one to about twenty four carbon atoms,
n is an integer having a value of two or more,
X is a leaving group as earlier described, and
Y is a negatively charged counterion.

When at least one of the three terminal substituents of the quaternary amine alkylating agent is a hydrophobic alkyl group having from four to about twenty-four carbons, the alkylating agent therefore provides both a hydrophobic moiety and a quaternary amine-containing moiety. The alkylene group in this instance is three or more carbon atoms in length.

Particular examples of quaternary ammonium compounds suitable as alkylating agents include the following:

(4-bromobutyl)diotylmethylammonium bromide;
(3-bromopropyl)dodecyldimethylammonium bromide;
(3-chloropropyl)dodecyldimethylammonium bromide;
(3-chloropropyl)decyldimethylammonium bromide;
(5-tosylpentyl)dodecyldimethylammonium bromide;
(6-bromohexyl)dimethyldecylammonium bromide;
(12-bromododecyl)decyldimethylammonium bromide;
(3-bromopropyl)tridecylammonium bromide;
(3-bromopropyl)docosyldimethylammonium bromide;
(6-bromohexyl)docosyldimethylammonium bromide;
(4-chlorobutyl)dodecyldimethylammonium bromide;
(3-chloropropyl)octadecyldimethylammonium bromide;
(3-bromopropyl)octyldimethylammonium bromide;
(4-iodobutyl)dioctylmethylammonium bromide;
(2,3-epoxy propyl)decyldimethylammonium bromide; and
(6-bromohexyl)docosyldimethyammonium bromide.

Other suitable alkylating agents include secondary and tertiary analogs, such as (3-bromobutyl) dioctylmethylammonium bromide and (3-chloro-3,3-dimethyl propyl)dioctylmethylammonium bromide.

Examples of suitable alkyl trimethylammonium alkylating agents include alkyl halide trimethylammonium salts, such as:

(4-halobutyl)trimethylammonium salt;
(5-halopentyl)trimethylammonium salt;
(6-halohexyl)trimethylammonium salt;
(7-haloheptyl)trimethylammonium salt;
(8-halooctyl)trimethylammonium salt;
(9-halononyl)trimethylammonium salt;
(10-halodecyl) trimethylammonium salt;
(11-haloundecyl)trimethylammonium salt;
(12-halododecyl)trimethylammonium salt; and combinations thereof. A particularly preferred quaternary amine-containing alkylating agent is (6-bromohexyl)- trimethylammonium bromide.

In another embodiment, the fat-binding polymer can be have a lipase inhibitor covalently bound to the polymer as described in U.S. Ser. No. 09/005,379 filed on Jan. 9, 1998, and Ser. No. 09/166,510 (Attorney Docket No. GTX96-11A), entitled "Lipase Inhibiting Polymers" being filed concurrently herewith, the entire contents of both of which are incorporated herein by reference. In a further embodiment, the fat-binding polymer can be administered in combination with a lipase inhibitor which is covalently bound to a polymer as described in U.S. Ser. No. 09/005,379 filed on Jan. 9, 1998, and Ser. No. 09/166,510 (Attorney Docket No. GTX96-11A) entitled "Lipase Inhibiting Polymers" being filed concurrently herewith, the entire contents of which are incorporated herein by reference.

As used herein, the terms "therapeutically effective amount" and "therapeutic amount" are synonymous. The terms refer to an amount which is sufficient to treat obesity, reduce the absorption of fat or treat hypertriglyceridemia. The dosage of fat-binding polymer administered to the patient will vary depending among other things on the weight of the patient and the general health of the patient. The dosage can be determined with regard to established medical practice. The amount of fat-binding polymer administered can be in the range of from about 0.01 mg/kg of body weight/day to about 1 g/kg of body weight/day. The amount of lipase inhibitor which can be administered in combination with the fat-binding polymers of the invention can be determined with regard to accepted medical practice.

As disclosed above, in a preferred embodiment, the fat-binding polymer is administered in combination with a lipase inhibitor, as described herein. The term "in combination" in this context includes both simultaneous or sequential administration (either type of compound first) of the fat-binding polymer and lipase inhibitor. The fat-binding polymer and lipase inhibitor, when used in combination, can be employed together in the same dosage form or in separate dosage forms taken at the same time or within a time period, wherein both the fat-binding polymer and lipase inhibitor are present in a therapeutically effective amount.

The fat-binding polymers of the invention can be formulated using conventional inert pharmaceutical adjuvant materials into dosage forms which are suitable for oral administration. The oral dosage forms include tablets, capsules, suspension, solutions, and the like. The identity of the inert adjuvant materials which are used in formulating the fat-binding polymers of the invention will be immediately apparent to persons skilled in the art. These adjuvant materials, either inorganic Or organic in nature, include, for example, gelatin, albumin, lactose, starch, magnesium stearate, preservatives (stabilizers), melting agents, emulsifying agents, salts, and buffers.

In patients with hypertriglyceridemia it is to be understood that the patient does not necessarily suffer from hypercholesterolemia.
Exemplifications

EXAMPLE 1

SYNTHESIS OF DIALLYLAMINE-HCL (DAA-HCL) SOLUTION

Diallylamine (DAA) (2000.3 g) was added slowly over a period of 2 days to concentrated HCl (2035.6 g). The temperature of the reaction was maintained below 10° C. by cooling the flask in an ice-salt-water bath, and by adjusting the addition rate. The room temperature pH of the resulting DAA-HCl solution (68.16% DAA-HCl) was 0.005.

EXAMPLE 2

POLYMERIZATION OF DIALLYLAMINE-HCL

To a 12-liter, 4-necked, round-bottomed flask equipped with an overhead stirrer and an air condenser was added DAA-HCl (3667.8 g of a 68.16% solution, and deionized water (4665.5 g). The resulting solution had a pH of 0.741. To the flask was added NaOH (66.8 g of a 50% aqueous solution). The resulting solution had a pH of 2.554. Nitrogen gas was bubbled through the solution, via a stainless steel needle, with stirring, and venting on top of the air condenser for 2 hours. The nitrogen line was put on top of the air condenser with positive pressure from a mineral oil bubbler. To the flask was added 125.0 g of freshly made 20% V-50 (Wako Chemicals USA, Inc., Richmond, Va.) in deionized water. This was added via syringe through a septum. The V-50 solution was not degassed with nitrogen. The solution was heated to 60° C. over a period of 1 hour and 8 minutes, with a heating mantle connected to a J-Kem temperature controller. The solution was heated at 60° C. for 18 hours. After the first 18 hour heating period, the reaction solution was allowed to cool down slowly to 49° C., and to the flask was added 125.0 g of freshly made 20% V-50 in deionized water. The solution was heated to 60° C. over a period of about 15 minutes, with a heating mantle connected to a J-Kem temperature controller. The solution was heated at 60° C. for 18 hours. After the second 18 hour heating period, the reaction solution was allowed to cool down slowly to 40° C., and to the flask was added 125.0 g of freshly made 20% V-50 in deionized water. The solution was heated to 60° C. over a period of about 15 minutes, with a heating mantle connected to a J-Kem temperature controller. The solution was heated at 60° C. for 18 hours. After cooling to room temperature, the solution was a dark orange viscous, flowable, clear solution. The flask contents were combined with deionized water (4166.7 g). The resulting solution had a pH of 4.4. SEC analysis: Mw 61494 Daltons; Polydispersity 2.43.

EXAMPLE 3

CROSSLINKING OF A SOLUBLE POLYMER TO OBTAIN A INSOLUBLE GEL; PREPARATION OF 3 MOL % CROSSLINKED POLY(ALLYLAMINE)HCL

Poly(allylamine) Hydrochloride (200 g of 50% aqueous solution, 1.07 mol monomer equivalents) was dissolved in a mixture of ethanol (213 mL) and water (125 mL) in a 1-liter, round-bottomed flask equipped with an overhead mechanical stirrer. The pH of the solution was brought to 10.0–10.2 by the addition of NaOH (50% solution). Epichlorohydrin (2.97 g, 32.07 mmol) was then added to the rapidly stirred solution in one portion. This mixture was stirred at room temperature (19–22° C.) until a gel formed (approx. 30 min), then stirring was suspended and the mixture was allowed to sit at room temperature for 20 hours. After the 20 hour reaction time had elapsed, the gel was transferred into a 5-liter bucket with 3 liters of deionized water. The mixture was then stirred with an overhead mechanical stirrer until the gel was well dispersed in solution. The pH was then adjusted to <1 using concentrated HCl. The mixture was then vacuum filtered through Whatman 541 filter paper. The filtered polymer gel was then collected and purified by suspension into 4 liters of deionized water followed by vacuum filtration through Whatman 541 filter paper. The procedure of suspension into deionized water followed by vacuum filtration was repeated several times until the conductivity of the suspended polymer gel was <0.5 mS/cm. After the final vacuum filtration, the polymer gel was transferred into several Pyrex drying trays and placed into a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mm Hg for at least 16 hours. Yield=83%.

TABLE 1

Epichlorohydrin Crosslinking Reactions Using a Procedure Similar to Example 3

| Example | Polyamine | mol % Xlink |
|---|---|---|
| 4 | Poly(allylamine) HCl | 6 |
| 5 | Poly(allylamine) HCl | 9 |

TABLE 1-continued

Epichlorohydrin Crosslinking Reactions Using a Procedure Similar to Example 3

| Example | Polyamine | mol % Xlink |
|---|---|---|
| 6 | Poly(allylamine) HCl 10 mol % C 12H 25 (prepared according to Example 82) | 3 |
| 7 | Polyethylenimine | 3 |
| 8 | Polyethylenimine | 6 |
| 9 | Poly(diallylamine) HCl | 3 |
| 10 | Poly(diallylamine) HCl | 4.5 |
| 11 | Poly(diallylamine) HCl | 6 |
| 12 | Poly(diallylmethylamine) HCl | 4.5 |
| 13 | Poly(vinylamine) | 4.5 |

EXAMPLE 14

LOW LEVEL CROSSLINKING OF A SOLUBLE POLYMER TO OBTAIN A HIGH MOLECULAR WEIGHT SOLUBLE POLYMER; PREPARATION OF 0.75 MOL % CROSSLINKED SOLUBLE POLY(ALLYLAMINE)HCL

Poly(allylamine) Hydrochloride (200 g of 50% aqueous solution, 1.07 mol monomer equivalents) was dissolved a mixture of ethanol (213 mL) and water (125 mL) in a 1-liter, round-bottomed flask equipped with an overhead mechanical stirrer. The pH of the solution was brought to 10.0–10.2 by the addition of NaOH (50% solution). Epichlorohydrin (743 mg, 8.03 mmol) was then added to the rapidly stirred solution in one portion at room temperature (19–22° C.). This mixture was stirred at room temperature (19–22° C.) for 20 hours. After the 20 hour reaction time had elapsed, the pH was adjusted to 11.5–12.0 by the addition of a 50% NaOH solution. The reaction mixture was then poured into a 5-liter beaker containing 2 liters of methanol stirred with an overhead mechanical stirrer. A fine precipitate was observed as this mixture was stirred for 30 minutes. The mixture was vacuum filtered through Whatman 541 filter paper, and the clear filtrate was acidified with concentrated HCl (pH<1) producing a thick polymer precipitate and a cloudy solution. The cloudy methanol solution was decanted away from the crude solid product. The precipitate was dissolved in a minimum amount of water (approx. 300 mL) and acidified with concentrated HCl to a pH of <2. The aqueous polymer solution was then poured with overhead mechanical stirring into a 3-liter beaker containing at least 5 volumes (approx. 1.5 liters) of methanol (Isopropanol can be used in place of methanol in this step). The polymeric product precipitated as a white solid. After stirring for 15 minutes, the precipitate was separated from solution by decantation and suspended in 2 liters of isopropyl alcohol. The solid was broken up using a metal spatula and the mixture was stirred for 2 hours. The isopropyl alcohol was then removed by decanting and the product was again suspended in 2liters of fresh isopropyl alcohol. After 2 hours of stirring, the solvent was decanted away and the solid product was placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours. Yield=88%.

EXAMPLE 15

PREPARATION OF 0.75 MOL % CROSSLINKED POLY(DIALLYLAMINE)HCL

Poly(diallylamine) Hydrochloride (3250 g of 20% aqueous solution, 4.86 mol monomer equivalents) was laced in a 20-liter bucket equipped with an over head mechanical stirrer. The pH of the solution was brought to 10.6 by the addition of NaOH (50% solution). Epichlorohydrin (2.86 mL, 0,037 mol) was then added to the rapidly stirred solution in one portion at room temperature (19–22° C.). This mixture was stirred at room temperature (19–22° C.) for 20 hours. A viscous solution resulted. Methanol (10 liters) was added, and the pH was adjusted to >11.5 using a 50% NaOH solution. This solution was then filtered to remove insoluble crosslinked polymer. The clear filtrate was acidified with concentrated HCl to a pH of <2, and the polymer product was precipitated with the addition of a large volume of ethanol. The solid was collected by decantation and washed with isopropanol. The solid product was then placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours. Yield=355 g

EXAMPLE 16

ALKYLATION OF AN INSOLUBLE GEL PREPARATION OF 10 MOL % DODECYL SUBSTITUTED, 3 MOL % CROSSLINKED POLY(ALLYLAMINE)HCL

Epichlorohydrin (3 mol %) crosslinked poly(allylamine) HCl (100 g of dry solid, 1.05 mol monomer equivalents) was suspended in methanol (1250 mL) in a 3-liter, round-bottomed flask equipped with an overhead mechanical stirrer, a condenser, and a thermocouple probe. Deionized water (750 mL) was slowly added to the suspension with good stirring, and the mixture was stirred until a uniform suspension resulted (approx. 3 hours). The mixture was then heated to 70° C., and the pH of the solution was brought to 10.0–10.2 by the addition of NaOH (50% solution). 1-Bromododecane (26.17 g, 0.105 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature and the pH was adjusted to <1 using concentrated HCl. The reaction mixture was then poured into a 5-liter beaker containing 3 liters of methanol stirred with an overhead mechanical stirrer. The mixture was stirred until a uniform suspension resulted. The mixture was then vacuum filtered through Whatman 541 filter paper. The filtered polymer gel was collected and suspended in 3 liters of fresh methanol. The methanol suspension was acidified to a pH of <1 with concentrated HCl. The mixture was then vacuum filtered through Whatman 541 filter paper. The filtered polymer gel was collected and suspended in 4-liters of 2M aqueous NaCl. The aqueous suspension was acidified to a pH of <1 with concentrated HCl. The mixture was then vacuum filtered through Whatman 541 filter paper. The filtered polymer gel was then collected and purified by suspension into 4 liters of deionized water followed by vacuum filtration through Whatman 541 filter paper. The procedure of suspension into deionized water followed by vacuum filtration was repeated several times until the conductivity of the suspended polymer gel was <0.5 mS/cm. After the final vacuum filtration, the polymer gel was transferred into several Pyrex drying trays and placed into a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours. Yield=82%.

TABLE 2

Alkylation Reactions of Xlinked Polyamines Using the Procedure in Example 16

| Example | Polyamine | Alkylating Agent | mol % |
|---|---|---|---|
| 17 | Poly(allylamine)HCl Xlink 3 mol % | 1-Bromohexane | 5 |
| 18 | Poly(allylamine)HCl Xlink 3 mol % | 1-Bromohexane | 10 |
| 19 | Poly(allylamine)HCl Xlink 3 mol % | 1-Bromohexane | 25 |
| 20 | Poly(allylamine)HCl Xlink 3 mol % | 1-Bromohexane | 50 |
| 21 | Poly(allylamine)HCl Xlink 3 mol % | 1-Bromooctane | 5 |
| 22 | Poly(allylamine)HCl Xlink 3 mol % | 1-Bromooctane | 10 |
| 23 | Poly(allylamine)HCl Xlink 3 mol % | 1-Bromooctane | 25 |
| 24 | Poly(allylamine)HCl Xlink 3 mol % | 1-Bromooctane | 50 |
| 25 | Poly(allylamine)HCl Xlink 3 mol % | 1-Bromododecane | 5 |
| 26 | Poly(allylamine)HCl Xlink 3 mol % | 1-Bromododecane | 25 |
| 27 | Poly(allylamine)HCl Xlink 3 mol % | 1-Bromododecane | 50 |
| 28 | Poly(allylamine)HCl Xlink 3 mol % | 1-Bromooctadecane | 5 |
| 29 | Poly(allylamine)HCl Xlink 3 mol % | 1-Bromooctadecane | 10 |
| 30 | Poly(allylamine)HCl Xlink 3 mol % | 1-Bromooctadecane | 25 |
| 31 | Poly(allylamine)HCl Xlink 3 mol % | 1-Bromo-2-ethylhexane | 5 |
| 32 | Poly(allylamine)HCl Xlink 3 mol % | 1-Bromo-2-ethylhexane | 10 |
| 33 | Poly(allylamine)HCl Xlink 3 mol % | 1-Bromo-2-ethylhexane | 25 |
| 34 | Poly(allylamine)HCl Xlink 3 mol % | 1-Bromo-2-ethylhexane | 50 |
| 35 | Poly(allylamine)HCl Xlink 3 mol % | (Bromomethyl)cyclohexane | 5 |
| 36 | Poly(allylamine)HCl Xlink 3 mol % | (Bromomethyl)cyclohexane | 10 |
| 37 | Poly(allylamine)HCl Xlink 3 mol % | (Bromomethyl)cyclohexane | 25 |
| 38 | Poly(allylamine)HCl Xlink 3 mol % | (3-Bromopropyl)trimethyl-ammonium Bromide | 5 |
| 39 | Poly(allylamine)HCl Xlink 3 mol % | (3-Bromopropyl)trimethyl-ammonium Bromide | 10 |
| 40 | Poly(allylamine)HCl Xlink 3 mol % | (3-Bromopropyl)trimethyl-ammonium Bromide | 25 |
| 41 | Poly(allylamine)HCl Xlink 3 mol % | (6-Bromohexyl)trimethyl-ammonium Chloride | 10 |
| 42 | Poly(allylamine)HCl Xlink 3 mol % | 1,3-Propane Sultone | 5 |
| 43 | Poly(allylamine)HCl Xlink 3 mol % | 1,3-Propane Sultone | 10 |
| 44 | Poly(allylamine)HCl Xlink 3 mol % | 1,3-Propane Sultone | 25 |
| 45 | Poly(allylamine)HCl Xlink 3 mol % | 1-Bromoacetic Acid | 5 |
| 46 | Poly(allylamine)HCl Xlink 3 mol % | 1-Bromoacetic Acid | 10 |
| 47 | Poly(allylamine)HCl Xlink 3 mol % | 1-Bromoacetic Acid | 25 |
| 48 | Poly(allylamine)HCl Xlink 3 mol % | 2-Bromoethanesulfonic Acid Na salt | 5 |
| 49 | Poly(allylamine)HCl Xlink 3 mol % | 2-Bromoethanesulfonic Acid Na salt | 10 |
| 50 | Poly(allylamine)HCl Xlink 3 mol % | 2-Bromoethanesulfonic Acid Na salt | 25 |
| 51 | Poly(allylamine)HCl Xlink 3 mol % | 2-Bromododecane (6-Bromohexyl)trimethylammonium Chloride | 10 10 |
| 52 | Poly(allylamine)HCl Xlink 6 mol % | 2-Bromododecane | 10 |
| 53 | Poly(allylamine)HCl Xlink 6 mol % | 2-Bromododecane (6-Bromohexyl)trimethylammonium Chloride | 10 10 |
| 54 | Poly(allylamine)HCl Xlink 3 mol % | (4-chlorobutyl)dodecyldimethylammonium Bromide | 10 |
| 55 | Poly(allylamine)HCl Xlink 3 mol % | (4-chlorobutyl)dodecyldimethylammonium Bromide | 40 |
| 56 | Poly(ethylenimine) Xlink 3 mol % | 1-Bromohexane | 5 |
| 57 | Poly(ethylenimine) Xlink 3 mol % | 1-Bromohexane | 10 |
| 58 | Poly(ethylenimine) Xlink 3 mol % | 1-Bromohexane | 25 |
| 59 | Poly(ethylenimine) Xlink 3 mol % | 1-Bromooctane | 5 |
| 60 | Poly(ethylenimine) Xlink 3 mol % | 1-Bromooctane | 10 |
| 61 | Poly(ethylenimine) Xlink 3 mol % | 1-Bromooctane | 25 |
| 62 | Poly(ethylenimine) Xlink 3 mol % | 1-Bromododecane | 5 |
| 63 | Poly(ethylenimine) Xlink 3 mol % | 1-Bromododecane | 10 |
| 64 | Poly(ethylenimine) Xlink 3 mol % | 1-Bromododecane | 25 |
| 65 | Poly(diallylamine)HCl Xlink 4.5 mol % | 1-Bromohexane | 5 |
| 66 | Poly(diallylamine)HCl Xlink 4.5 mol % | 1-Bromohexane | 25 |
| 67 | Poly(diallylamine)HCl Xlink 4.5 mol % | 1-Bromohexane | 50 |
| 68 | Poly(diallylamine)HCl Xlink 4.5 mol % | 1-Bromooctane | 5 |
| 69 | Poly(diallylamine)HCl Xlink 4.5 mol % | 1-Bromooctane | 30 |
| 70 | Poly(diallylamine)HCl Xlink 4.5 mol % | 1-Bromooctane | 40 |
| 71 | Poly(diallylamine)HCl Xlink 4.5 mol % | 1-Bromododecane | 5 |
| 72 | Poly(diallylamine)HCl Xlink 4.5 mol % | 1-Bromododecane | 11 |
| 73 | Poly(diallylamine)HCl Xlink 4.5 mol % | 1-Bromododecane | 25 |
| 74 | Poly(diallylamine)HCl Xlink 4.5 mol % | (4-chlorobutyl)dodecyldimethylammonium Bromide | 10 |
| 75 | Poly(diallylamine)HCl Xlink 4.5 mol % | (4-chlorobutyl)dodecyldimethylammonium Bromide | 20 |
| 76 | Poly(diallylamine)HCl Xlink 4.5 mol % | (4-chlorobutyl)dodecyldimethylammonium Bromide | 30 |

EXAMPLE 77

ACETYLATION OF A CROSSLINKED POLYMER GEL PREPARATION OF 25 MOL % ACETYLATED-POLY(ALLYLAMINE)HCL

Epichlorohydrin (3 mol %) crosslinked poly(allylamine) HCl (57.4 g of dry solid, 0.602 mol monomer equivalents) was suspended in methanol (1 liter) in a 2-liter, round-bottomed flask equipped with an overhead mechanical stirrer, a condenser, and a thermocouple probe. Deionized water (550 mL) was slowly added to the suspension with good stirring, and the mixture was stirred until a uniform suspension resulted (approx. 3 hours). The mixture was then cooled to 15° C. with an ice bath, and the pH of the solution was brought to 9.5 by the addition of NaOH (50% solution). Acetic anhydride (15.41 g, 0.151 mol) was then added to the stirred solution in one portion. This mixture was stirred at 15° C. for 30 minutes. The solution pH was maintained at 9.5 during this time by the addition of small quantities of 50% NaOH. After the 30 minutes it was observed that the pH of the mixture was stable. The crude polymer product was then purified by suspension into 4 liters of deionized water followed by vacuum filtration through Whatman 541 filter paper. The procedure of suspension into deionized water followed by vacuum filtration was repeated several times until the conductivity of the suspended polymer gel was <1 mS/cm. The polymer gel was then suspended in deionized water (2 liters) and the mixture was acidified with concentrated HCl to a pH of <2.5. The mixture was then filtered and transferred into several Pyrex drying trays. The trays were placed into a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours. Yield =49.9 g

TABLE 3

Acetylation reactions according to the procedure Of Example 77

| Example | Polyamine | mol % Acetylation |
| --- | --- | --- |
| 78 | Poly(allylamine) HCl | 50 |
| 79 | Poly(diallylamine) HCl | 25 |
| 80 | Poly(diallylamine) HCl | 50 |
| 81 | Poly(diallylamine) HCl | 100 |

EXAMPLE 82

ALKYLATION OF A SOLUBLE POLYMER PREPARATION OF 10 MOL % DODECYL-POLY (ALLYLAMINE)HCL

Poly(allylamine) Hydrochloride (200 g of 50% aqueous solution, 1.07 mol monomer equivalents) was dissolved a mixture of ethanol (213 mL) and water (125 mL), and was heated to 70° C. in a 1-liter, round-bottomed flask equipped with an overhead mechanical stirrer, a condenser, and a thermocouple probe. The pH of the solution was brought to 10.0–10.2 by the addition of NaOH (50% solution). 1-Bromododecane (26.66 g, 0.107 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature and the pH was adjusted to 11.5–12.0 by the addition of a 50% NaOH solution. The reaction mixture was then poured into a 5-liter beaker containing 2 liters of methanol stirred with an overhead mechanical stirrer. A fine precipitate was observed as this mixture was stirred for 30 minutes. The mixture was vacuum filtered through Whatman 541 filter paper, and the clear filtrate was acidified with concentrated HCl (pH <1) producing a thick polymer precipitate and a cloudy solution. The cloudy methanol solution was decanted away from the crude solid product. The precipitate was dissolved in a minimum amount of water (approx. 300 mL) and acidified with concentrated HCl to a pH of <2. The aqueous polymer solution was then poured with overhead mechanical stirring into a 3-liter beaker containing at least 5 volumes (approx. 1.5 liters) of methanol (isopropanol can be used in place of methanol in this step). The polymeric product precipitated as a white solid. After stirring for 15 minutes, the precipitate was separated from solution by decantation and suspended in 2 liters of isopropyl alcohol. The solid was broken up using a metal spatula and the mixture was stirred for 2 hours. The isopropyl alcohol was then removed by decanting and the product was again suspended in 2 liters of fresh isopropyl alcohol. After 2 hours of stirring, the solvent was decanted away and the solid product was placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours. Yield=86%.

EXAMPLE 83

PREPARATION OF 0.75 MOL % CROSSLINKED, 10 MOL % HEXYL-POLY (ALLYLAMINE) HCL

The procedure of Example 82 was used. The 50% aqueous solution of poly(allylamine)HCl was replaced with an equivalent amount of a 50% aqueous solution of the polymer product of Example 14. In place of the 1-bromododecane, 1-bromohexane (17.66 g, 0.107 mol) was used.

EXAMPLE 84

PREPARATION OF 0.75 MOL % CROSSLINKED, 10 MOL % DODECYL-POLY (ALLYLAMINE) HCL

The procedure of Example 82 was used. The 50% aqueous solution of poly(allylamine)HCl was replaced with an equivalent amount of a 50% aqueous solution of the polymer product of Example 14.

EXAMPLE 85

PREPARATION OF 0.75 MOL % CROSSLINKED, 2 MOL % OCTADECYL-POLY (ALLYLAMINE) HCL

The procedure of Example 82 was used. The 50% aqueous solution of poly(allylamine)HCl was replaced with an equivalent amount of a 50% aqueous solution of the polymer product of Example 14. In place of the 1-bromododecane, 1-bromooctadecane (7.13 g, 0.021 mol) was used.

EXAMPLE 86

PREPARATION OF 0.75 MOL % CROSSLINKED, 25 MOL % DODECYL-POLY (ALLYLAMINE)HCL

The procedure of Example 82 was used. The amount of dodecyl bromide used was 67.3 g, 0.27 mol. The 50% aqueous solution of poly(allylamine)HCl was replaced with an equivalent amount of a 50% aqueous solution of the polymer product of Example 14.

EXAMPLE 87

PREPARATION OF 25 MOL % HEXYL-POLY (ALLYLAMINE)HCL 0.75 MOL % EPICHLOROHYDRIN CROSSLINKED

Poly(allylamine) Hydrochloride 0.75% epichlorohydrin crosslinked from Example 14 (200 g of 50% aqueous solution, 1.07 mol monomer equivalents) was dissolved in a mixture of ethanol (213 mL) and water (125 mL), and was heated to 70° C. in a 1-liter, round-bottomed flask equipped with an overhead mechanical stirrer, a condenser, and a thermocouple probe. The pH of the solution was brought to 10.0–10.2 by the addition of NaOH (50% solution). 1-Bromohexane (44.2 g, 0.27 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature and the pH was adjusted to 11.5–12.0 by the addition of a 50% NaOH solution. The reaction mixture was then poured into a 5-liter beaker containing 2 liters of methanol stirred with an overhead mechanical stirrer. In this case, no precipitate was formed. The methanol solution was evaporated to dryness giving a stick solid. The solid was dissolved in 800 mL of methanol and 3 liters of hexane was added to precipitate the polymer. After collection by filtration, the polymeric solid was washed with an additional 1 liter of hexane and collected by filtration. The solid product was placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.
Yield=89.3 g

EXAMPLE 88

PREPARATION OF 50 MOL % HEXYL-POLY (ALLYLAMINE)HCL 0.75 MOL % EPICHLOROHYDRIN CROSSLINKED

Poly(allylamine) Hydrochloride 0.75% epichlorohydrin crosslinked from Example 14 (200 g of 50% aqueous solution, 1.07 mol monomer equivalents) was dissolved in a mixture of ethanol (213 mL) and water (125 mL), and was heated to 70° C. in a 1-liter, round-bottomed flask equipped with an overhead mechanical stirrer, a condenser, and a thermocouple probe. The pH of the solution was brought to 10.0–10.2 by the addition of NaOH (50% solution). 1-Bromohexane (88.4 g, 0.51 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature giving a white suspension of polymer. The white solid was allowed to settle, and the solution was decanted away. Deionized water (1.5 liters) was added and the slurry was stirred for 15 minutes. The solid was allowed to settle and the solution was removed by decantation. The solid was then dissolved in 800 mL of isopropanol. Concentrated HCl (120 mL) was added but no precipitate was seen. Hexane (3 liters) was added and a white solid precipitated from solution. After collection by filtration, the polymeric solid was washed with an additional 1.5 liters of hexane and collected by filtration. The solid product was placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.
Yield=117 g

EXAMPLE 89

PREPARATION OF 5 MOL % DODECYL-POLY (ALLYLAMINE)HCL 0.75 MOL % EPICHLOROHYDRIN CROSSLINKED

Poly(allylamine) Hydrochloride 0.75% epichlorohydrin crosslinked from Example 14 (200 g of 50% aqueous solution, 1.07 mol monomer equivalents) was dissolved in a mixture of ethanol (213 mL) and water (125 mL), and was heated to 70° C. in a 1-liter, round-bottomed flask equipped with an overhead mechanical stirrer, a condenser, and a thermocouple probe. The pH of the solution was brought to 10.0–10.2 by the addition of NaOH (50% solution). 1-Bromododecane (13.33 g, 0.054 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature and the pH was adjusted to 11.5–12.0 by the addition of a 50% NaOH solution. The reaction mixture was then poured into a 5-liter beaker containing 2 liters of methanol stirred with an overhead mechanical stirrer. A fine precipitate was observed as this mixture as stirred for 30 minutes. The mixture was vacuum filtered through Whatman 541 filter paper, and the clear filtrate was acidified with concentrated HCl (pH<1) producing a thick polymer precipitate and a cloudy solution. The cloudy methanol solution was decanted away from the crude solid product. Isopropanol (2.5 liters) was added and the solid was broken into small pieces with a spatula. The solid was collected by decantation and washed a second time with fresh isopropanol. The solid product was placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.
Yield=81 g

EXAMPLE 90

PREPARATION OF 5 MOL % OCTADECYL-POLY(ALLYLAMINE)HCL 0.75 MOL % EPICHLOROHYDRIN CROSSLINKED

Poly(allylamine) Hydrochloride 0.75% epichlorohydrin crosslinked from Example 14 (200 g of 50% aqueous solution, 1.07 mol monomer equivalents) was dissolved a mixture of ethanol (213 mL) and water (125 mL), and was heated to 70° C. in a 1-liter, round-bottomed flask equipped with an overhead mechanical stirrer, a condenser, and a thermocouple probe. The pH of the solution was brought to 10.0–10.2 by the addition of NaOH (50% solution). 1-Bromooctadecane (17.84 g, 0.054 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature and poured into a 5-liter beaker containing 2 liters of methanol stirred with an overhead mechanical stirrer. The mixture was acidified with concentrated HCl (pH<1) producing a thick polymer precipitate. The methanol solution was decanted away from the crude solid product, and water (approx. 300 mL) was added to disperse the polymeric product into a slurry. Methanol (900 mL) was added giving a dense precipitate. The solution was decanted away and the polymer was slurried in water a second time and precipitated with methanol. The solid polymer was then washed with 2.5 liters of isopropanol, and then with I liter of diethyl ether. The solid product was then placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.
Yield=111 g

EXAMPLE 91

PREPARATION OF 10 MOL % OCTADECYL-POLY(ALLYLAMINE)HCL 0.75 MOL % EPICHLOROHYDRIN CROSSLINKED

The procedure of Example 90 was used. The amount of octadecyl bromide used was 35.67 g, 0.107 mol.
Yield=124 g

EXAMPLE 92

PREPARATION OF 5 MOL % DOCOSYL-POLY(ALLYLAMINE)HCL 0.75 MOL % EPICHLOROHYDRIN CROSSLINKED

The procedure of Example 90 was used. The amount of docosyl bromide used was 21.03 g, 0.054 mol.
Yield=96 g

EXAMPLE 93

PREPARATION OF 10 MOL % DOCOSYL-POLY(ALLYLAMINE)HCL 0.75 MOL % EPICHLOROHYDRIN CROSSLINKED

The procedure of Example 90 was used. The amount of docosyl bromide used was 41.68 g, 0.107 mol.
Yield=101 g

EXAMPLE 94

PREPARATION OF 25 MOL % HEXYL-POLYETHYLENIMINE HCL

Polyethylenimine (200 g of a 50% aqueous solution from Aldrich Chemical Co., 2.32 mol monomer equivalents) was dissolved a mixture of ethanol (213 mL) and water (125 mL), and was heated to 70° C. in a 1-liter, round-bottomed flask equipped with an overhead mechanical stirrer, a condenser, and a thermocouple probe. 1-Bromohexane (95.7 g, 0.58 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature and poured into a 20-liter bucket containing 3 liters of methanol stirred with an overhead mechanical stirrer. The mixture was acidified with concentrated HCl (pH<2), but no precipitate was formed. Isopropanol (6 liters) was added, giving a small amount of precipitate. Diethyl ether was then added (3 liters) and the crude product precipitated. The solvent was decanted away from the product. The crude product was then redispersed in 750 mL of deionized water. The pH was adjusted to <2 using concentrated HCl. Acetonitrile (5 liters) was then added to precipitate the polymer. The solid was collected by decantation and washed with 2 liters of isopropanol. The solid product was then placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.
Yield=172 g

EXAMPLE 95

PREPARATION OF 50 MOL % HEXYL-POLYETHYLENIMINE HCL

Polyethylenimine (200 g of a 50% aqueous solution from Aldrich Chemical Co., 2.32 mol monomer equivalents) was dissolved in a mixture of ethanol (213 mL) and water (125 mL), and was heated to 70° C. in a 1-liter, round-bottomed flask equipped with an overhead mechanical stirrer, a condenser, and a thermocouple probe. 1-Bromohexane (191.5 g, 1.16 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20-hour reaction time had elapsed, the mixture was cooled to room temperature and poured into a 20-liter bucket containing 2 liters of methanol stirred with an overhead mechanical stirrer. The mixture was acidified with concentrated HCl (pH<2), but no precipitate was formed. Diethyl ether was then added (3 liters) and the crude product precipitated. The solvent was decanted away from the product. The crude product was then redispersed in ethanol (3 liters). The pH was adjusted to >11.5 using concentrated NaOH. The free base polymer dissolved, leaving a suspension of salts. The mixture was vacuum filtered through Whatman 541 filter paper, and the clear filtrate was acidified with concentrated HCl (pH<1). Diethyl ether was then added to precipitate the product, which was then collected by decantation. The solid product was then placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.
Yield=110 g

EXAMPLE 96

PREPARATION OF 5 MOL % DODECYL-POLYETHYLENIMINE HCL

Polyethylenimine (200 g of a 50% aqueous solution from Aldrich Chemical Co., 2.32 mol monomer equivalents) was dissolved in a mixture of ethanol (213 mL) and water (125 mL), and was heated to 70° C. in a 1-liter, round-bottomed flask equipped with an overhead mechanical stirrer, a condenser, and a thermocouple probe. 1-Bromododecane (28.9 g, 0.116 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature and poured into a 20-liter bucket containing 2 liters of methanol stirred with an overhead mechanical stirrer. The mixture was acidified with concentrated HCl (pH<2), resulting in the precipitation of some polymer. Isopropanol was then added (3 liters) and the crude product precipitated. The solvent was decanted away from the product. The crude product was then redispersed in water (750 mL) and methanol (400 mL) and the pH was adjusted to <2 using concentrated HCl. Isopropanol (6 liters) was then added to precipitate the product, which was collected by decantation. The solid product was then placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.

Yield=146 g

EXAMPLE 97

PREPARATION OF 10 MOL % DODECYL-POLYETHYLENIMINE HCL

Polyethylenimine (200 g of a 50% aqueous solution from Aldrich Chemical Co., 2.32 mol monomer equivalents) was dissolved in a mixture of ethanol (213 mL) and water (125 mL), and was heated to 70° C. in a 1-liter, round-bottomed flask equipped with an overhead mechanical stirrer, a condenser, and a thermocouple probe. 1-Bromododecane (57.8 g, 0.232 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature and poured into a 20-liter bucket containing 2 liters of methanol stirred with an overhead mechanical stirrer. The mixture was acidified with concentrated HCl (pH<2), resulting in the precipitation of some polymer. Isopropanol was then added (3 liters) and the crude product precipitated. The solvent was decanted away from the product. The crude product was then redispersed in water (750 mL) and methanol (400 mL) and the pH was adjusted to <2 using concentrated HCl. Isopropanol (6 liters) was then added to precipitate the product, which was collected by decantation. The solid product was then placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.

Yield=119 g

EXAMPLE 98

PREPARATION OF 25 MOL % DODECYL-POLYETHYLENIMINE HCL

Polyethylenimine (200 g of a 50% aqueous solution from Aldrich Chemical Co., 2.32 mol monomer equivalents) was dissolved in a mixture of ethanol (213 mL) and water (125 mL), and was heated to 70° C. in a 1-liter, round-bottomed flask equipped with an overhead mechanical stirrer, a condenser, and a thermocouple probe. 1-Bromododecane (144.6 g, 0.58 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature and poured into a 20-liter pail containing 5 liters of ethanol stirred with an overhead mechanical stirrer. The mixture was acidified with concentrated HCl (pH<2), resulting in the precipitation of the crude product. The solvent was decanted, and the crude product was then redissolved in water (750 mL). The pH was adjusted to <2 using concentrated HCl. Isopropanol (6 liters) was then added to precipitate the product, which was collected by decantation. The solid product was then placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.

Yield=197 g

EXAMPLE 99

PREPARATION OF 2.5 MOL % OCTADECYL-POLYETHYLENIMINE HCL

Polyethylenimine (200 g of a 50% aqueous solution from Aldrich Chemical Co., 2.32 mol monomer equivalents) was dissolved in a mixture of ethanol (213 mL) and water (125 mL), and was heated to 70° C. in a 1-liter, round-bottomed flask equipped with an overhead mechanical stirrer, a condenser, and a thermocouple probe. 1-bromooctadecane (19.3 g, 0.058 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was .cooled to room temperature and poured into a 20-liter bucket containing 3.5 liters of methanol stirred with an overhead mechanical stirrer. The mixture was acidified with concentrated HCl (pH<2), resulting in the precipitation of the crude product. The solvent was decanted, and the crude product was then redissolved in water (1100 mL). The pH was adjusted to <2 using concentrated HCl. Isopropanol (6 liters) was then added to precipitate the product, which was collected by decantation. The solid was washed with another 2 liters of clean isopropanol and collected by decantation. The solid product was then placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.

Yield=169g

EXAMPLE 100

PREPARATION OF 5 MOL % OCTADECYL-POLYETHYLENIMINE HCL

The procedure of Example 99 was used. The amount of 1-bromooctadecane used 38.7 g, 0.116 mol.

Yield=198 g

EXAMPLE 101

PREPARATION OF 2 MOL % DOCOSYL-POLYETHYLENIMINE HCL

Polyethylenimine (200 g of a 50% aqueous solution from Aldrich Chemical Co., 2.32 mol monomer equivalents) was dissolved in a mixture of ethanol (213 mL) and water (125 mL), and was heated to 70° C. in a 1-liter, round-bottomed flask equipped with an overhead mechanical stirrer, a condenser, and a thermocouple probe. 1-Bromodocosane (18.1 g, 0.046 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature and poured into a 20-liter bucket containing 2.4 liters of ethanol stirred with an overhead mechanical stirrer. The mixture was acidified with concentrated HCl (pH<2), resulting in the precipitation the crude product. The solvent was decanted, and the crude product was then redissolved in water (700 mL). The pH was adjusted to <2 using concentrated HCl. Isopropanol (6 liters) was then added to precipitate the product, which was collected by decantation. The solid was washed with another 2 liters of clean isopropanol and collected by decantation. The solid product was then placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.
Yield=154 g

EXAMPLE 102

PREPARATION OF 5 MOL % DOCOSYL-POLYETHYLENIMINE HCL

The procedure of Example 101 was used. The amount of 1-bromodocosane used was 45.2 g, 0.116 mol.
Yield=160 g

EXAMPLE 103

PREPARATION OF 5 MOL % DODECYL-POLY(DIALLYLAMINE)HCL 0.75 MOL % EPICHLOROHYDRIN CROSSLINKED

Poly(diallylamine) Hydrochloride 0.75% epichlorohydrin crosslinked from Example 15 (60 g, 0.45 mol monomer equivalents) was dispersed in ethanol (500 mL) in a 1-liter, round-bottomed flask equipped with an overhead mechanical stirrer, a condenser, and a thermocouple probe. NaOH was added (30 g of a 50% solution), along with deionized water (200 mL) and the mixture was heated to 70° C. The pH of the solution was brought to 10.0–10.2 by the addition of NaOH (50% solution). 1-Bromododecane (5.6 g, 0.023 mol) was then added to the stirred solution in one portion. This mixture was stirred at 70° C. for 20 hours. The solution pH was checked periodically during this time, and was maintained at 10.0–10.2 by the addition of small quantities of 50% NaOH. After the 20 hour reaction time had elapsed, the mixture was cooled to room temperature and poured into a 5-liter beaker containing 3 liters of deionized water stirred with an overhead mechanical stirrer. The crude polymeric product precipitated from solution and was collected by decantation. The crude product was added to a mixture of 300 mL deionized water and 300 mL ethanol. The mixture was acidified with concentrated HCl (pH<1) and stirred for at least 2 hours. Isopropanol (3 liters) was then added to precipitate the product. The solid polymer was then washed with clean isopropanol (2 liters). The solid product was then placed in a convection oven at 70° C. to dry (24–48 hours). The dried solid was ground to a fine powder using a lab mill with stainless steel blades, and was passed through a sieve (50 mesh) to remove large granules. The ground product was then placed in a vacuum oven at 60° C. and 28 mmHg for at least 16 hours.
Yield=27 g

EXAMPLE 104

PREPARATION OF 10 MOL % DODECYL-POLY(DIALLYLAMINE)HCL 0.75 MOL % EPICHLOROHYDRIN CROSSLINKED

The procedure of Example 104 was used. The amount of 1-bromododecane used was 11.2 g, 0.045 mol.
Yield=46 g

EXAMPLE 105

PREPARATION OF 25 MOL % DODECYL-POLY(DIALLYLAMINE)HCL 0.75 MOL % EPICHLOROHYDRIN CROSSLINKED

The procedure of Example 104 was used. The amount of 1-bromododecane used was 28.2 g, 0.113 mol.
Yield=52 g

EXAMPLE 106

PREPARATION OF 5 MOL % HEXYL-POLY(DIALLYLAMINE)HCL 0.75 MOL % EPICHLOROHYDRIN CROSSLINKED

The procedure of Example 104 was used. The amount of 1-bromohexane used was 3.72 g, 0.023 mol.

EXAMPLE 107

PREPARATION OF 10 MOL % HEXYL-POLY(DIALLYLAMINE)HCL 0.75 MOL % EPICHLOROHYDRIN CROSSLINKED

The procedure of Example 104 was used. The amount of 1-bromohexane used was 7.43 g, 0.045 mol.
Yield=36 g

EXAMPLE 108

PREPARATION OF 25 MOL % HEXYL-POLY(DIALLYLAMINE)HCL 0.75 MOL % EPICHLOROHYDRIN CROSSLINKED

The procedure of Example 104 was used. The amount of 1-bromohexane used was 18.65 g, 0.113 mol.
Yield=49 g

EXAMPLE 109

PREPARATION OF 50 MOL % HEXYL-POLY(DIALLYLAMINE)HCL 0.75 MOL % EPICHLOROHYDRIN CROSSLINKED

The procedure of Example 104 was used. The amount of 1-bromohexane used was 38.0 g, 0.230 mol.
Yield=67 g

EXAMPLE 110

PREPARATION OF 2 MOL % OCTADECYL-POLY(DIALLYLAMINE)HCL 0.75 MOL % EPICHLOROHYDRIN CROSSLINKED

The procedure of Example 104 was used. The amount of 1-bromooctadecane used was 3.0 g, 0.009 mol.
Yield=23 g

EXAMPLE 111

PREPARATION OF 5 MOL % OCTADECYL-POLY(DIALLYLAMINE)HCL 0.75 MOL % EPICHLOROHYDRIN CROSSLINKED

The procedure of Example 104 was used. The amount of 1-bromooctadecane used was 7.7 g, 0.023 mol.

Yield=35 g

EXAMPLE 112

PREPARATION OF 10 MOL % OCTADECYL-POLY(DIALLYLAMINE)HCL 0.75 MOL % EPICHLOROHYDRIN CROSSLINKED

The procedure of Example 104 was used. The amount of 1-bromooctadecane used was 15.0 g, 0.045 mol.
Yield=35 g

EXAMPLE 113

PREPARATION OF COPOLYMER OF ACRYLAMIDE (20 MOLE %)/ TRIMETHYLAMINOETHYL ACRYLCHLORIDE Q SALT (TMAEAC) (78 MOLE %)/ OCTADECYLACRYLATE (2 MOLE %)

To a 1-liter, three-necked flask equipped with condenser and stir bar, were added trimethylaminoethyl acrylchloride quaternary salt (TMAEAC) 50% aqueous solution (150.90 g of 50% solution, 390 mmoles, 78 mole %), acrylamide (7.11 g, 100 mmoles, 20 mole %), octadecyl acrylate ( 3.25 g, 10 mmoles, 2 mole %) and isopropanol (400 mL). The mixture was purged with nitrogen for 10 min before the addition of a radical initiator, AIBN (330 mg, 2 mmoles). The mixture was heated to 70° C. for 16 hours. At the end of the 16 hour reaction time, the reaction mixture was allowed to cool to room temperature and poured into a beaker containing isopropanol (1 liter). The polymer was precipitated out as a white solid, which was collected and ground to small pieces in a blender using isopropanol as a solvent. The pieces were collected by filtration and the polymer was dried under vacuum at 60° C. for 2 days. The material was ground to a fine powder (82 g), which was used for the in vitro and in vivo studies.

The following polymers of Table 4 with varying composition of acrylamide, TMAEAC and octadecyl acrylate were prepared using the above procedure.

TABLE 4

| Example No. | Acrylamide (mole %) | TMAEAC (mole %) | Octadecyl acrylate (mole %) |
|---|---|---|---|
| 114 | 20 | 75 | 5 |
| 115 | 20 | 70 | 10 |
| 116 | 35 | 63 | 2 |
| 117 | 35 | 60 | 5 |
| 118 | 35 | 55 | 10 |
| 119 | 50 | 48 | 2 |
| 120 | 50 | 45 | 5 |
| 121 | 50 | 40 | 10 |
| 122 | 0 | 98 | 2 |
| 123 | 0 | 95 | 5 |
| 124 | 0 | 90 | 10 |

EXAMPLE 125

PREPARATION OF COPOLYMER OF ACRYLAMIDE (20 MOLE %) TRIMETHYLAMINOETHYL ACRYLCHLORIDE Q SALT (TMAEAC) (75 MOLE %)/ DODECYLACRYLATE (5 MOLE %)

To a 1-liter, three-necked flask equipped with condenser and stir bar, were added trimethylaminoethyl acrylchloride quaternary salt (TMAEAC) 50% aqueous solution (145.80 g of 50% solution, 375 mmoles, 75 mole %), acrylamide (7.11 g, 100 mmoles, 20 mole %), dodecyl acrylate (6.01 g, 25 mmoles, 5 mole %) and isopropanol 400 mL). The mixture was purged with nitrogen for 10 min before the addition of a radical initiator, AIBN (330 mg, 2 mmoles). The mixture was heated to 70° C. for 16 hours. The reaction mixture was allowed to cool to room temperature and poured into a beaker containing isopropanol (1 liter). The polymer was precipitated out as a white solid, which was collected and ground to small pieces in a blender using isopropanol as a solvent. The pieces were collected by filtration and the polymer was dried under vacuum at 60° C. for 2 days. The material was ground to a fine powder (80 g), which was used for the in vitro and in vivo studies. The polymers of Table 5 were prepared using the above procedure.

TABLE 5

| Example No. | Acrylamide (mole %) | TMAEAC (mole %) | Dodecylacrylate (mole %) |
|---|---|---|---|
| 126 | 20 | 70 | 10 |
| 127 | 20 | 55 | 25 |
| 128 | 35 | 60 | 5 |
| 129 | 35 | 55 | 10 |
| 130 | 35 | 40 | 25 |
| 131 | 50 | 45 | 5 |
| 132 | 50 | 40 | 10 |
| 133 | 50 | 25 | 25 |
| 134 | 0 | 95 | 5 |
| 135 | 0 | 90 | 10 |
| 136 | 0 | 75 | 25 |
| 137 | 0 | 98 | 2 |
| 138 | 20 | 78 | 2 |
| 139 | 35 | 63 | 2 |
| 140 | 50 | 48 | 2 |

EXAMPLE 141

PREPARATION OF COPOLYMER OF ACRYLAMIDE (20 MOLE %)TRIMETHYLAMINOETHYL ACRYLCHLORIDE Q SALT (TMAEAC) (80 MOLE %)

To a 1-liter, three-necked flask equipped with condenser and stir bar, were added trimethylaminoethyl acrylchloride quaternary salt (TMAEAC) 50% aqueous solution (154.76 g of 50% solution, 400 mmoles, 80 mole %), acrylamide (7.1 g, 100 mmoles, 20 mole %), and isopropanol (400 mL). The mixture was purged with nitrogen for 10 min before the addition of a radical initiator, AIBN ( 330 mg, 2 mmoles). The mixture was heated to 70° C. for 16 hours. At the end of reaction, reaction mixture was allowed to cool to room temperature and poured into a beaker containing isopropanol (1 liter). The polymer was precipitated out as a white solid, which was collected and ground to small pieces in a blender using isopropanol as a solvent. The pieces were collected by filtration and the polymer was dried under vacuum at 60° C. for 2 days. The material was ground to a fine powder (80 g), which was used for the in vitro and in vivo studies.

The polymers of Table 6 were prepared using the above procedure

TABLE 6

| Example No. | Acrylamide (mole %) | TMAEAC (mole %) |
|---|---|---|
| 142 | 0 | 100 |
| 143 | 10 | 90 |
| 141 | 20 | 80 |

TABLE 6-continued

| Example No. | Acrylamide (mole %) | TMAEAC (mole %) |
|---|---|---|
| 144 | 35 | 65 |
| 145 | 50 | 50 |

EXAMPLE 146

PREPARATION OF METHYLENEBISACRYLAMIDE (4 MOLE %) CROSS-LINKED POLYMERS OF ACRYLAMIDE (20 MOLE %)/TRIMETHYLAMINOETHYL ACRYLCHLORIDE Q SALT (TMAEAC) (78 MOLE %)/ OCTADECYL ACRYLATE (2 MOLE %)

To a 1-liter, three-necked flask equipped with condenser and stir bar, were added trimethylaminoethyl acrylchloride quaternary salt (TMAEAC) 50% aqueous solution (150.90 g of 50% solution, 390 mmoles, 78 mole %), acrylamide (7.11 g, 100 mmoles, 20 mole %), octadecyl acrylate ( 3.25 g, 10 mmoles, 2 mole %), methylenebisacrylamide (3.08 g, 20 mmoles, 4 mole %) and ethanol (300 mL) were added. The mixture was purged with nitrogen for 10 min before the addition of a radical initiator, AIBN (330 mg, 2 mmoles). The mixture was heated to 70° C. for 16 hours. At the end of reaction, reaction mixture was allowed to cool to room temperature and poured into a beaker containing isopropanol (1 liter). The polymer was precipitated out as a white solid, which was collected and ground to small pieces in a blender using isopropanol as a solvent. The pieces were collected by filtration and the polymer was dried under vacuum at 60° C. for 2 days. The material was ground to a fine powder (84 g), which was used for the in vitro and in vivo studies.
The compounds of Table 7 were prepared using the above procedure.

TABLE 7

| Example No. | Acrylamide (mole %) | TMAEAC (mole %) | Octadecyl acrylate (mole %) | Methylenebisacrylamide (mole %) |
|---|---|---|---|---|
| 147 | 20 | 75 | 5 | 4 |
| 148 | 20 | 70 | 10 | 4 |
| 149 | 35 | 63 | 2 | 4 |
| 150 | 35 | 60 | 5 | 4 |
| 151 | 35 | 55 | 10 | 4 |
| 152 | 50 | 48 | 2 | 4 |
| 153 | 50 | 45 | 5 | 4 |
| 154 | 50 | 40 | 10 | 4 |
| 155 | 0 | 98 | 2 | 4 |
| 156 | 0 | 95 | 5 | 4 |
| 157 | 0 | 90 | 10 | 4 |

EXAMPLE 158

PREPARATION OF METHYLENEBISACRYLAMIDE (4 MOLE %) CROSS-LINKED POLYMER OF ACRYLAMIDE (20 MOLE %)/TRIMETHYLAMINOETHYL ACRYLCHLORIDE Q SALT (TMAEAC) (75 MOLE %)/DODECYLACRYLATE (5 MOLE %)

To a 1-liter, three-necked flask equipped with condenser and stir bar, were added trimethylaminoethyl acrylchloride quaternary salt (TMAEAC) 50% aqueous solution (145.80 g of 50% solution, 375 mmoles, 75 mole %), acrylamide (7.11 g, 100 mmoles, 20 mole %), dodecylacrylate (6.01 g, 25 mmoles, 5 mole %), methylenebisacrylamide (3.08 g, 20 mmoles, 4 mole %) and ethanol (300 mL). The mixture was purged with nitrogen for 10 min before the addition of a radical initiator, AIBN (330 mg, 2 mmoles). The mixture was heated to 70° C. for 16 hours. The reaction mixture was allowed to cool to room temperature and poured into a beaker containing isopropanol (1 liter). The polymer was precipitated out as a white solid, which was collected and ground to small pieces in a blender using isopropanol as a solvent. The pieces were collected by filtration and the polymer was dried under vacuum at 60° C. for 2 days. The material was ground to a fine powder (80 g), which was used for the in vitro and in vivo studies. The following cross-linked polymers were prepared.
The polymers of Table 8 were prepared using the above procedure.

TABLE 8

| Example No. | Acrylamide (mole %) | TMAEAC (mole %) | Dodecylacrylate (mole %) | Methylene-bisacrylamide (mole %) |
|---|---|---|---|---|
| 159 | 20 | 70 | 10 | 4 |
| 160 | 20 | 55 | 25 | 4 |
| 161 | 35 | 60 | 5 | 4 |
| 162 | 35 | 55 | 10 | 4 |
| 163 | 35 | 40 | 25 | 4 |
| 164 | 50 | 45 | 5 | 4 |
| 165 | 50 | 40 | 10 | 4 |
| 166 | 50 | 25 | 25 | 4 |
| 167 | 0 | 95 | 5 | 4 |
| 168 | 0 | 90 | 10 | 4 |
| 169 | 0 | 75 | 25 | 4 |

EXAMPLE 170

PREPARATION OF COPOLYMER OF METHACRYLAMIDE (20 MOL %)/ TRIMETHYLAMINOETHYL METHACHLORIDE QUATERNARY SALT (TMAEMC) (78 MOL %)/OCTADECYL METHACRYLATE (2 MOL %)

To a 1 liter, three necked, round-bottomed flask equipped with condenser, stir bar, heating mantle (with J-Kem temperature controller) and nitrogen bubbler was added: trimethylammonioethyl methacrylate chloride (TMAEMC) ~75% aqueous 87.19 g (420.39 mmol), octadecyl methacrylate (3.65 g, 10.80 mmol), methacrylamide (9.16 g, 107.76 mmol), and ethanol (300 mL). The total amount of monomer solids should be 100 g. Nitrogen was allowed to bubble through the room temperature monomer mixture for at least 20 minutes before adding 0.275 g AIBN [2,2'-azobis(2-methyl-propionitrile)]. At this point the nitrogen was set to blanket the mixture and the heat was turned on to 70° C. The reaction was allowed to heat for 22 hours at 70° C. While the polymer was still warm it was poured from the flask into a Nalgene bucket and allowed to stand for at least three hours in each of four 1-liter washings of isopropanol. Once the polymer became slightly rigid/rubbery it was broken up into small chunks using a blender (with isopropanol as the liquid). The granular product was filtered and washed with more isopropanol and placed in a crystallizing dish in a 70° C. convection oven for two days. After this time, the product was removed and ground to a fine powder using a grinder and placed back in the oven for two more days. GPC analysis of octadecyl methacrylate containing polymers shows MW ranges form 100K–150K with polydispersities ranging from 2.5–5. The following table gives general mole percent compositions of polymers prepared in this fashion.

The polymers of Table 9 were prepared using the above procedure.

TABLE 9

| Example No. | Methacrylamide (mole %) | TMAEMC (mole %) | Octadecyl Methacrylate (mole %) |
|---|---|---|---|
| 171 | 0 | 98 | 2 |
| 172 | 0 | 95 | 5 |
| 173 | 0 | 90 | 10 |
| 174 | 0 | 85 | 15 |
| 175 | 0 | 80 | 20 |
| 170 | 20 | 78 | 2 |
| 176 | 20 | 75 | 5 |
| 177 | 20 | 70 | 10 |
| 178 | 35 | 63 | 2 |
| 179 | 35 | 60 | 5 |
| 180 | 35 | 55 | 10 |
| 181 | 50 | 48 | 2 |
| 182 | 50 | 45 | 5 |
| 183 | 50 | 40 | 10 |

EXAMPLE 184

PREPARATION OF COPOLYMER OF METHACRYLAMIDE (20 MOL %)/ TRIMETHYLAMINOETHYL METHACRY-CHLORIDE QUATERNARY SALT (TMAEMC) (75 MOL %)/DODECYL METHACRYLATE (5 MOL %)

To a 1-liter, three-necked, round-bottomed flask equipped with condenser, stir bar, heating mantle (with J-Kem temperature controller) and nitrogen bubbler was added: trimethylammonioethyl methacrylate chloride (TMAEMC) ~75% aqueous (83.97 g, 404.86 mmol), dodecyl methacrylate (6.85 g, 26.96 mmol), methacrylamide (9.18 g, 108.0 mmol), and ethanol (300 mL). The total amount of monomer solids should be 100 g. Nitrogen was allowed to bubble through the room temperature monomer mixture for at least 20 minutes before adding 0.275 g AIBN [2,2'-azobis(2-methyl-propionitrile)]. At this point, the nitrogen was set to blanket the mixture and the heat was turned on to 70° C. The reaction was allowed to heat for 22 hours at 70° C. While the polymer was still warm it was poured from the flask into a Nalgene bucket and allowed to stand for at least three hours in each of four 1-liter washings of isopropanol. Once the polymer became slightly rigid/rubbery it was broken up into small chunks using a blender (with isopropanol as the liquid). The granular product was filtered and washed with more isopropanol and placed in a crystallizing dish in a 70° C. convection oven for two days. After this time, the product was removed and ground to a fine powder using a grinder and placed back in the oven for two more days. GPC analysis of dodecyl methacrylate containing polymers shows MW ranges form 170–190K with polydispersities ranging from 2.3–2.8. Table 10 gives general mole percent compositions of polymers prepared in this fashion.

The polymers of Table 10 were prepared using the above procedure.

TABLE 10

| Example No. | Methacrylamide (mole %) | TMAEMC (mole %) | Dodecyl metrhacrylate (mole %) |
|---|---|---|---|
| 185 | 0 | 95 | 5 |
| 186 | 0 | 90 | 10 |
| 187 | 0 | 75 | 25 |
| 184 | 20 | 75 | 5 |
| 188 | 20 | 70 | 10 |
| 189 | 20 | 55 | 25 |
| 190 | 35 | 60 | 5 |
| 191 | 35 | 55 | 10 |
| 192 | 35 | 40 | 25 |
| 193 | 50 | 45 | 5 |
| 194 | 50 | 40 | 10 |
| 195 | 50 | 25 | 25 |

EXAMPLE 196

PREPARATION OF COPOLYMER OF TMAEMC (80 MOL %)/METHACRYLAMIDE (20 MOL %)

To a 1 liter, three-necked, round-bottomed flask equipped with condenser, stir bar, heating mantle (with J-Kem temperature controller) and nitrogen bubbler was added: trimethylammonioethyl methacrylate chloride (TMAEMC) ~75% aqueous, (90.71 g, 437.36 mmol), methacrylamide (9.29 g, 109.29 mmol), and ethanol (300 mL). The total amount of monomer solids should be 100 g. Nitrogen was allowed to bubble through the room temperature monomer mixture for at least 20 minutes before adding 0.275 g AIBN [2,2'-azobis(2-methyl-propionitrile)]. At this point, the nitrogen was set to blanket the mixture and the heat was turned on to 70° C. The reaction was allowed to heat for 22 hours at 70° C. While the polymer was still warm it was poured from the flask into a Nalgene bucket and allowed to stand for at least three hours in each of four 1-liter washings of isopropanol. Once the polymer became slightly rigid/rubbery it was broken up into small chunks using a blender (with isopropanol as the liquid). The granular product was filtered and washed with more isopropanol and placed in a crystallizing dish in a 70° C. convection oven for two days. After this time the product was removed and ground to a fine powder using a grinder and placed back in the oven for two more days. Table 11 gives general mole percent compositions of polymers prepared in this fashion.

The polymers of Table 11 were prepared using the above procedure.

TABLE 11

| Example No. | Methacrylamide (mole %) | TMAEMC (mole %) |
|---|---|---|
| 197 | 0 | 100 |
| 196 | 20 | 80 |
| 198 | 35 | 65 |
| 199 | 50 | 50 |

EXAMPLE 200

PREPARATION OF METHACRYLATE METHYLENEBISMETHACRYLAMIDE (2MOLE %) CROSS-LINKED POLYMER OF METHACRYLAMIDE (20 MOL %)/TMAEMC (78 MOL %)/OCTADECYL METHACRYLATE (2 MOL %)

To a 1 liter, three-necked, two-part reaction flak equipped with condenser, mechanical stirrer, water bath, and nitrogen bubbler was added trimethylammonioethyl methacrylate chloride (TMAEMC), 75% aqueous (87.19 g, 420.39 mmol) octadecyl methacrylate (3.65 g,10.80 mmol), methacrylamide (9.16 g, 107.76 mmol), and ethanol (400 mL). The total amount of monomer solids should be 100 g. To this was added an additional 2 mole percent (of total monomers) N,N'-methylenebismethacrylamide (1.96 g, 10.76 mmol). Nitrogen was allowed to bubble through the room temperature monomer mixture for at least 20 minutes before adding 0.275 g AIBN [2,2'-azobis(2-methyl-propionitrile)]. At this point, the nitrogen was set to blanket the mixture and the heat was turned on to 70° C. Once the polymer began to gel the stirring was turned off; total heating time at 70° C. was approximately 5 hours. The polymer was then allowed cool down to room temperature and stand overnight. The gelled product was scooped out of the flask and swollen to a clear gel in a 500 mL isopropanol/ 1000 mL water mixture. The gel was washed 6X with 1000 mL isopropanol filtering over a 50-mesh sieve. Once the polymer became slightly rigid/ rubbery it was broken up into small chunks using a blender (with isopropanol as the liquid). The product was filtered over a sieve, wrung out, and placed in a drying dish in a 70° C. convection oven for two days. After this time, the product was removed and ground to a fine powder using a grinder and placed back in the oven for two more days in a glass crystallizing dish. Table 12 gives general mole percent compositions of polymers prepared in this fashion.

The polymers of Table 12 were prepared using the above procedure.

TABLE 12

| Example No. | Meth-acrylamide (mole %) | TMAEMC (mole %) | Octadecyl Methacrylate (mole %) | Methylenebis-methacrylamide (mole %) |
| --- | --- | --- | --- | --- |
| 201 | 0 | 98 | 2 | 2 |
| 202 | 0 | 95 | 5 | 2 |
| 203 | 0 | 90 | 10 | 2 |
| 204 | 0 | 85 | 15 | 2 |
| 205 | 0 | 80 | 20 | 2 |
| 200 | 20 | 78 | 2 | 2 |
| 206 | 20 | 75 | 5 | 2 |
| 207 | 20 | 70 | 10 | 2 |
| 208 | 35 | 63 | 2 | 2 |
| 209 | 35 | 60 | 5 | 2 |
| 210 | 35 | 55 | 10 | 2 |
| 211 | 50 | 48 | 2 | 2 |
| 212 | 50 | 45 | 5 | 2 |
| 213 | 50 | 40 | 10 | 2 |

EXAMPLE 214

PREPARATION OF METHACRYLATEMETHYLENE-BISMETHACRYLAMIDE (2MOLE %) CROSS-LINED POLYMER OF METHACRYLAMIDE (20 MOL %)/TMAEMC (75 MOL %)/ DODECYL METHACRYLATE (5 MOL %)

To a 1-liter, three-necked, two-part reaction flask equipped with condenser, mechanical stirrer, water bath, and nitrogen bubbler was added: trimethylammonioethyl methacrylate chloride (TMAEMC), 75% aqueous solution (83.97 g, 404.86 mmol), dodecyl methacrylate (6.85 g, 26.96 mmol), methacrylamide (9.18g, 108.0 mmol) and ethanol (400 mL). The total amount of monomer solids should be 100 g. To this was added an additional 2 mole percent (of total monomers) N,N'-methylenebismethacrylamide (1.96 g, 10.79 mmol). Nitrogen was allowed to bubble through the room temperature monomer mixture for at least 20 minutes before adding 0.275 g AIBN [2,2'-azobis(2-methyl-propionitrile)]. At this point, the nitrogen was set to blanket the mixture and the heat was turned on to 70° C. Once the polymer began to gel the stirring was turned off; total heating time at 70° C. was approximately 5 hours. The polymer was then allowed cool down to room temperature and stand overnight. The gelled product was scooped out of the flask and swollen to a clear gel in a 500 mL isopropanol/ 1000 mL water mixture. The gel was washed 6X with 1000 mL of isopropanol filtering over a 50-mesh sieve. Once the polymer became slightly rigid/rubbery it was broken up into small chunks using a blender (with isopropanol as the liquid). The product was filtered over a sieve, wrung out, and placed in a drying dish in a 70° C. convection oven for two days. After this time, the product was removed and ground to a fine powder using a grinder and placed back in the oven for two more days in a glass crystallizing dish. Table 13 gives general mole percent compositions of polymers prepared in this fashion.

TABLE 13

| Example No. | Methacryl-amide (mole %) | TMAEC (mole %) | Dodecyl methacrylate (mole %) | Methylenebis-methacrylamide (mole %) |
| --- | --- | --- | --- | --- |
| 215 | 0 | 95 | 5 | 2 |
| 216 | 0 | 90 | 10 | 2 |
| 217 | 0 | 75 | 25 | 2 |
| 214 | 20 | 75 | 5 | 2 |
| 218 | 20 | 70 | 10 | 2 |
| 219 | 20 | 55 | 25 | 2 |
| 220 | 35 | 60 | 5 | 2 |
| 221 | 35 | 55 | 10 | 2 |
| 222 | 35 | 40 | 25 | 2 |
| 223 | 50 | 45 | 5 | 2 |
| 224 | 50 | 40 | 10 | 2 |
| 225 | 50 | 25 | 25 | 2 |

EXAMPLE 226

PREPARATION OF METHACRYLATEMETHYLENEBISMETHA CRYLAMIDE (2MOLE %) CROSS-LINKED POLYMER OF METHACRYLAMIDE (20 MOL %)/TMAEMC (80 MOL %)

To a 1-liter, three-necked, two-part reaction flask equipped with condenser, mechanical stirrer, water bath, and nitrogen bubbler was added: trimethylammonioethyl methacrylate chloride (TMAEMC) 75% aqueous solution (90.71 g, 437.36 mmol), methacrylamide 9.29 g (109.29 mmol), and ethanol (400 mL). The total amount of monomer solids should be 100 g. To this was added an additional 2 mole percent (of total monomers) N,N'-methylenebismethacrylamide (1.989 g, 10.93 mmol). Nitrogen was allowed to bubble through the room temperature monomer mixture for at least 20 minutes before adding 0.275 g AIBN [2,2'-azobis(2-methyl-propionitrile)]. At this point, the nitrogen was set to blanket the mixture and the heat was turned on to 70° C. Once the polymer began to gel the stirring is turned off; total heating time at 70° C. was approximately 5 hours. The polymer was then allowed cool down to room temperature and stand overnight. The gelled product was scooped out of the flask and swollen to a clear gel in a 500 mL isopropanol/ 1000 mL of water mixture. The gel was washed 6xwith 1000 mL isopropanol filtering over a 50-mesh sieve. Once the polymer became slightly rigid/rubbery it was broken up into small chunks using a blender (with isopropanol as the liquid). The spongy product is filtered over a sieve, pressed dry, and placed in a drying dish in a 70° C. convection oven for two days. After this time the product was removed and ground to a fine powder using a grinder and placed back in the oven for two more days in a glass crystallizing dish. Table 14 gives general mole percent compositions of polymers prepared in this fashion.

TABLE 14

| Example No. | Methacrylamide (mole %) | TMAEMC (mole %) | Methylenebismeth- Acrylamide (mole %) |
|---|---|---|---|
| 227 | 0 | 100 | 2 |
| 226 | 20 | 80 | 2 |
| 228 | 35 | 65 | 2 |
| 229 | 50 | 50 | 2 |

METHOD FOR DETERMINING BINDING OF EMULSION PARTICLES BY LIPID- BINDING POLYMERS USING AN OLIVE OIL EMULSION WITH PHYSIOLOGICAL EMULSIFIERS
PREPARATION OF OLIVE OIL EMULSION FOR LIPID-BINDING ASSAY
EMULSIFIER SOLUTION

Egg yolk lecithin 2.54 mmol (2.00 g) and cholesterol 1.25 mmol (0.483 g) were dissolved in 100 mL of chloroform in a 1-liter, round-bottomed flask and the solvent was removed rapidly using a rotary evaporator. A coating of lecithin and cholesterol resulted, adhering to the walls of the flask. This film was held under vacuum for 12 hours. The sodium salts of the following bile acids were then added to the flask: glycocholic 1.217 g (2.496 mmol), taurocholic 0.895 g (1.664 mmol), glycodeoxycholic 1.766 g (3.744 mmol), taurodeoxycholic 1.302 g (2.496 mmol). An aqueous buffer consisting of 0.1M 2-[N-morpholino]ethanesulfonic acid (MES) and 0.1M sodium chloride was prepared and the pH was adjusted with 50% NaOH to pH=6.5. 1 liter of this aqueous buffer was added to the flask containing the coating of lecithin and cholesterol, and this mixture was stirred for 3–4 hours. During this time, the coating of lecithin and cholesterol was dispersed in solution. A cloudy solution resulted.
EMULSION In a 400 mL, thick-walled beaker, were mixed highly refined acid free olive oil 31.49 g, and oleic acid 3.51 g. The emulsifier solution described above was then added to bring the total weight of the mixture to 350 g. A 1-inch drying coated stir bar was added, and the mixture was stirred magnetically for 2–5 minutes. The mixture was then irradiated with 2 bursts of ultrasound (45 sec. each, with 2 minutes of magnetic stirring between bursts) using a Branson Sonifier 450 operated at maximum power with a ¾" solid horn. The pH of the resulting emulsion was adjusted to 6.5 (at 20° C.). The emulsion prepared in this way was used immediately in the fat binding test, but could be kept in a refrigerator (4° C.) for a week.

When the physiological emulsion described above was mixed with test polymers, it was observed that a solid polymer/lipid complex would form in some cases. A test was devised to measure the quantity of lipid absorbed by the test polymers from the physiological emulsion.
LIPID BINDING TEST The test polymer (25 mg) was weighed into a tared 20 mL centrifuge filter cup with a 10 micron polypropylene mesh filter (Whatman VECTASPIN20™ centrifuge filter). The bottom of the filter cup was then sealed with tape to prevent solution from leaking out during the test. Using an analytical pipette, an aqueous buffer solution (3 mL) containing NaCl (0.1M), and MES (0.1M) at pH=6.5 was added to the filter cup. The filter cup was inserted into its companion centrifuge tube and sealed with a cap. This assembly was agitated in an orbital shaker for at least 1 hour in order to dissolve or disperse the test polymer. The olive oil emulsion described above (15 mL) was then added to the filter cup using an analytical pipette. The cap was replaced, and the centrifuge tube shaken (250 rpm) on an orbital mixer for a period of one hour. The centrifuge filter device was then disassembled so that the tape could be removed from the bottom of the centrifuge filter cup. It was immediately reassembled and spun in a centrifuge at an RCF of 500 G, and at 25° C. for 30 minutes. The centrifuge filter device was removed from the centrifuge and disassembled. The filter cup was weighed to obtain the weight gain of the wet polymer/lipid complex. This material was the removed from the filter cup with a spatula, and placed into a tared glass vial. The vial was weighed again to obtain the weight of the polymer/lipid sample. The vial was then placed into a centrifugal evaporator, and dried at 60° C. under vacuum until a pressure of 0.15 Torr or less was achieved (8–18 hrs). The vial was removed and weighed to obtain the dry weight of the polymer/lipid complex sample. The amount of lipid absorbed by the original 25 mg polymer sample in the filter cup was then calculated. This gravimetric result was used as a measure for lipid binding by the polymer, and is listed in the accompanying table as lipid weight absorbed (g) per gram of polymer.

TABLE 15

| EXAMPLE No. | Lipid weight (g) absorbed by 1 gram of polymer |
|---|---|
| Chitosan | 2.2 |
| 10 | 5.5 |
| 13 | 6.8 |
| 14 | 20 |
| 15 | 44.9 |
| 16 | 3.4 |
| 52 | 3.3 |
| 54 | 4.6 |
| 55 | 3.8 |
| 66 | 5.9 |
| 67 | 5.9 |
| 69 | 4.5 |
| 70 | 4.1 |
| 72 | 5.8 |
| 75 | 4.5 |
| 76 | 3.9 |
| 78 | 3 |
| 79 | 3.6 |
| 80 | 12.6 |
| 81 | 3.1 |
| 83 | 10 |
| 84 | 2.7 |
| 85 | 11.3 |
| 86 | 2.1 |
| 87 | 6.5 |
| 88 | 3.1 |
| 89 | 6.9 |
| 90 | 4.5 |
| 91 | 6.2 |
| 92 | 10.9 |
| 94 | 2.8 |
| 96 | 4.7 |
| 97 | 4.5 |
| 98 | 1.7 |
| 99 | 5.7 |
| 100 | 3.3 |
| 101 | 11 |
| 102 | 13.4 |
| 103 | 4.3 |

TABLE 15-continued

| EXAMPLE No. | Lipid weight (g) absorbed by 1 gram of polymer |
|---|---|
| 104 | 16 |
| 105 | 2.1 |
| 107 | 7.7 |
| 108 | 6.6 |
| 109 | 5.1 |
| 110 | 6.1 |
| 111 | 4.8 |
| 112 | 3.8 |
| 113 | 60 |
| 114 | 58 |
| 115 | 58 |
| 116 | 59 |
| 117 | 59 |
| 118 | 60 |
| 119 | 54 |
| 120 | 59 |
| 121 | 60 |
| 122 | 56 |
| 123 | 54 |
| 124 | 50 |
| 125 | 59 |
| 126 | 52 |
| 127 | 56 |
| 128 | 66 |
| 129 | 62 |
| 130 | 60 |
| 131 | 59 |
| 132 | 58 |
| 133 | 59 |
| 134 | 49 |
| 135 | 49 |
| 136 | 43 |
| 137 | 57 |
| 138 | 64 |
| 140 | 63 |
| 141 | 66 |
| 166 | 48 |
| 167 | 59 |
| 168 | 61 |
| 169 | 39 |
| 172 | 61 |
| 173 | 33 |
| 174 | 39 |
| 175 | 65 |
| 176 | 15 |
| 177 | 37 |
| 178 | 21 |
| 179 | 24 |
| 180 | 57 |
| 181 | 68 |
| 182 | 60 |
| 183 | 51 |
| 184 | 65 |
| 185 | 7 |
| 186 | 67 |
| 187 | 27 |
| 188 | 2 |
| 189 | 43 |
| 190 | 10 |
| 191 | 2 |
| 192 | 68 |
| 193 | 67 |
| 194 | 61 |
| 195 | 64 |
| 196 | 16 |
| 197 | 8 |
| 198 | 13 |
| 199 | 5 |
| 202 | 9 |
| 203 | 6 |
| 204 | 15 |
| 205 | 7 |
| 206 | 3 |
| 207 | 22 |
| 208 | 4 |
| 209 | 3 |

IN VIVO TESTING OF FAT-BINDING POLYMERS

The non-crosslinked and crosslinked fat-binding polymers of Examples 5, 6, 10, 72, 173 and Chitosan were evaluated for their ability to increase the excretion of fat in the feces, relative to the control group, in normal rats over a six-day period. Male Sprague-Dawley rats (five to six weeks of age) were individually housed and fed ad libitum a powdered "high-fat diet," consisting of standard rodent chow supplemented with 15% lard by weight. After feeding the animals this diet for five days, the animals were weighed and sorted into the treatment or control groups (4–6 animals per group, each group having equal mean body weights). Animals were treated for six days with the test compounds, which were added to the "high-fat diet" at concentrations (w/w) of 0.0% (control), 2.0 or 5.0 percent of the diet. In one study chitosan was evaluated for its effect on fecal fat excretion.

Rat fecal samples were collected on the final three days of the six days of drug treatment. The samples were freeze dried and ground to a fine powder. One half gram of sample was weighed and transferred to extraction cells. Samples were extracted in an accelerated solvent extractor (ASE 200 Accelerated Solvent Extractor, Dyonex Corporation, Sunnyvale, Calif.) with 95% ethanol, 5% water and 100 mM KOH. The sample was extracted in 17 minutes at 150° C. and 1500 psi. An aliquot of extract was transferred to a test tube containing a molar excess of HCl. The sample was then evaporated and reconstituted in a detergent solution consisting of 2% Triton X-1200, 1% polyoxyethylene lauryl ether and 0.9% NaCl. Fatty acids were then quantitated enzymatically with a calorimetric kit (NEFAC, Wako Chemical GmbH, Neuss, Germany).

Table 16 contains values for fecal fat excretion as a percentage of ingested fat.

TABLE 16

IN VIVO EFFICACY OF FAT-BINDING POLYMERS

| Example Identification | Dose (w/w percent of diet) | FECAL FAT EXCRETION % OF INGESTED FAT |
|---|---|---|
| Example 6-PAA 3% XL, 10% C12 | 5 | 40 |
| Example 6-PAA 3% XL, 10% C12 | 2 | 12 |
| Example 5-PAA 9.4% XL | 2 | 22 |
| Example 10-PDA 4.5% XL | 2 | 30 |
| Example 72-PDA 4.5% XL, 11% C12 | 2 | 29 |
| Example 173-TMAEMC (90 mol %) + octadecyl methacrylate(10 mol %) | 2 | 20 |
| Chitosan | 2 | 8 |

Fecal Fat/Consumed Fat was calculated as follows: Fatty acid concentration from the enzymatic assay was expressed as mmol/mL. The mmol/mL of fatty acid was then multiplied by the number of mL of extract generated from 500 mg of sample to give the total mmol of fatty acid. The value for the total mmol of fatty acid was converted to total mg of fatty acid using the average molecular weight of medium to long chain fatty acid (270 D). The value was corrected for any dilutions made during sample workup. When results are expressed as mg/gm of feces, the total mg of fatty acids is multiplied by 2. When results were expressed as total mg of fatty acid excreted in 24 hours, the mg/gm of feces value was multiplied by fecal weight in grams excreted in 24 hours. When the results were expressed as excreted fat as a % of that consumed in 24 hours, the total weight of fat excreted in 24 hours was divided by the weight of fatty acids consumed over 24 hours and multiplied by 100.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method for treating obesity in a mammal, comprising the step of orally administering to the mammal an effective amount of one or more fat-binding polymers in combination with one or more lipase inhibitors, wherein the fat-binding polymer is selected from the group consisting of polyalkylacrylates, polyacrylamides, polyalkylmethacrylates, polymethacrylamides, poly-N-alkylacrylamides, poly-N-alkylmethacrylamides, substituted derivatives thereof and copolymers thereof.

2. The method of claim 1 wherein the fat-binding polymer is poly(dimethylamino propylacrylamide), poly(trimethylammonium ethylacrylate), poly(trimethylammoniumethyl methacrylate), poly(trimethylammoniumpropyl acrylamide), poly(dodecyl acrylate), poly(octadecyl acrylate), poly(octadecyl methacrylate) or copolymers thereof.

3. The method of claim 1 wherein the polymer is crosslinked by a multifunctional co-monomer.

4. The method of claim 3 wherein the amount of crosslinking agent is between about 0.5 and about 25 weight percent based on the combined weight of crosslinking agent and monomers.

5. The method of claim 3 wherein the multifunctional co-monomer is selected from the group consisting of diacrylates, triacrylates, tetraacrylates, dimethacrylates, diacrylamides, dimethacrylamides, diallylacrylamides and polyvinylarenes.

6. The method of claim 5 wherein the multifunctional comonomer is selected from the group consisting of ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), bisphenol A dimethacrylate, bisphenol A diacrylate, pentaerythritol tetraacrylate, trimethylolpropane triacrylate and divinylbenzene.

7. A method for treating obesity in a mammal comprising the step of orally administering to the mammal an effective amount of one or more fat-binding polymers in combination with one or more lipase inhibitors, wherein the fat-binding polymer is a synthetic amine polymer.

8. The method of claim 7 wherein the amine polymer further comprises one or more hydrophobic regions comprising an alkyl group of between about four and about twenty-four carbons, and one or more positively charged regions comprising a quaternary amine-containing moiety having the following formula:

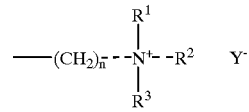

$R^1$, $R^2$ and $R^3$ represent an alkyl group, wherein each R, independently, is a normal or branched, substituted or unsubstituted, normal, branched or cyclic alkyl group having a carbon atom chain length of between about one to about twenty-four carbon atoms;

n is an integer having a value of three or more; and

Y is a negatively-charged counterion.

9. The method of claim 7 wherein the amine polymer is selected from the group consisting of poly(allylamine), poly(ethyleneimine), poly(vinylamine), poly(diallylamine), and poly(diallylmethylamine).

10. The method of claim 9 wherein the amine polymer is crosslinked by means of a multifunctional crosslinking agent, said agent being present in an amount from about 0.5%–25% weight, based upon the combined weight of monomer and crosslinking agent.

11. The method of claim 7 wherein the amine polymer further comprises one or more hydrophobic regions bound to a portion of the amine nitrogens.

12. The method of claim 11 wherein the hydrophobic regions are bound to between about 1 and about 60 percent of the amine nitrogens.

13. The method of claim 12 wherein the hydrophobic regions are bound to between about 1 and about 30 percent of the amine nitrogens.

14. The method of claim 11 wherein the hydrophobic region is a substituted or unsubstituted, normal, branched or cyclic alkyl group having at least four carbons.

15. The method of claim 14 wherein the hydrophobic region is an alkyl group of between about four and thirty carbons.

16. The method of claim 15 wherein the hydrophobic region is an alkyl group of about 6 carbons.

17. The method of claim 15 wherein the hydrophobic region is an alkyl group of about 8 carbons.

18. The method of claim 15 wherein the hydrophobic region is an alkyl group of about 10 carbons.

19. The method of claim 15 wherein the hydrophobic region is an alkyl group of about 12 carbons.

20. The method of claim 15 wherein the hydrophobic region is an alkyl group of about 18 carbons.

21. The method of claim 7 wherein the amine polymer further comprises one or more positively charged regions bound to a portion of the amine nitrogens.

22. The method of claim 21 wherein the positively charge region comprises a quaternary amine-containing moiety having the following formula:

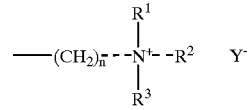

$R^1$, $R^2$ and $R^3$ represent hydrogen or an alkyl group, wherein each R, independently, is a normal or branched, substituted or unsubstituted, normal, branched or cyclic alkyl group having a carbon atom chain length of between about one to about twenty-four carbon atoms;

n is an integer having a value of three or more; and

Y is a negatively-charged counterion.

23. A method for treating obesity in a mammal, comprising the step of orally administering to the mammal an effective amount of one or more fat-binding polymers in combination with one or more lipase inhibitors, wherein the fat-binding polymer comprises a monomer of the formula:

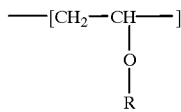

wherein R is —H or a hydrophobic region.

24. The method of claim 23 wherein the hydrophobic region comprises a substituted or unsubstituted, normal, branched or cyclic alkyl group having at least about four carbons.

25. The method of claim 23 wherein the hydrophobic region comprises an alkyl group of between about four and thirty carbons.

26. The method of claim 23 wherein the hydrophobic region comprises an alkyl group of about 6 carbons.

27. A method for treating obesity in a mammal, comprising the step of orally administering to the mammal an effective amount of one or more fat-binding polymers in combination with one or more lipase inhibitors, wherein the fat-binding polymer is substituted with a lipase inhibitor.

28. A method for reducing the absorption of dietary fat in a mammal, comprising the step of orally administering to the mammal a therapeutic amount of one or more fat-binding polymers in combination with one or more lipase inhibitors wherein the fat-binding polymer is selected from the group consisting of polyalkylacrylates, polyacrylamides, polyalkylmethacrylates, polymethacrylamides, poly-N-alkylacrylamides, poly-N-alkylmethacrylamides, substituted derivatives thereof and copolymers thereof.

29. A method for treating obesity in a mammal, comprising the step of orally administering to the mammal an effective amount of one or more fat-binding polymers, wherein the fat-binding polymer is selected from the group consisting of polyalkylacrylates, polyacrylamides, polyalkylmethacrylates, polymethacrylamides, poly-N-alkylacrylamides, poly-N-alkylmethacrylamides, substituted derivatives thereof and copolymers thereof.

30. A method for treating obesity in a mammal, comprising the step of orally administering to the mammal an effective amount of one or more fat-binding polymers in combination with one or more lipase inhibitors, wherein the fat-binding polymer is selected from the group consisting of polyalkylacrylates, polyacrylamides, polyalkylmethacrylates, polymethacrylamides, poly-N-alkylacrylamides, poly-N-alkylmethacrylamides, substituted derivatives thereof and copolymers thereof, and wherein the lipase inhibitor is selected from lipstatin, tetrahydrolipstatin or a combination thereof.

31. A method for treating obesity in a mammal, comprising the step of orally administering to the mammal an effective amount of one or more fat-binding polymers, wherein the fat-binding polymer is substituted with a lipase inhibitor.

* * * * *